US007425431B2

(12) United States Patent
Church et al.

(10) Patent No.: US 7,425,431 B2
(45) Date of Patent: Sep. 16, 2008

(54) POLONY FLUORESCENT IN SITU SEQUENCING BEADS

(75) Inventors: George M. Church, Brookline, MA (US); Jay Shendure, Chagrin Falls, OH (US); Gregory J. Porreca, Cambridge, MA (US); Jun Zhu, Durham, NC (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 11/505,073

(22) Filed: Aug. 16, 2006

(65) Prior Publication Data

US 2007/0087362 A1   Apr. 19, 2007

Related U.S. Application Data

(63) Continuation of application No. PCT/US05/06425, filed on Feb. 28, 2005.

(60) Provisional application No. 60/548,631, filed on Feb. 27, 2004.

(51) Int. Cl.
C12P 19/34 (2006.01)
C12N 15/11 (2006.01)

(52) U.S. Cl. .......................... 435/91.1; 536/23.1; 435/6

(58) Field of Classification Search .................. None
See application file for complete search history.

(56) References Cited

U.S. PATENT DOCUMENTS

| | | | |
|---|---|---|---|
| 4,659,774 A | 4/1987 | Webb et al. | 525/54.2 |
| 4,861,571 A | 8/1989 | Harada et al. | 423/709 |
| 5,141,813 A | 8/1992 | Nelson | 428/402 |
| 5,264,566 A | 11/1993 | Froehler et al. | 536/25.34 |
| 5,428,148 A | 6/1995 | Reddy et al. | 536/26.8 |
| 5,554,744 A | 9/1996 | Bhongle et al. | 536/25.3 |
| 5,574,146 A | 11/1996 | Reddy et al. | 536/25.34 |
| 5,602,244 A | 2/1997 | Caruthers et al. | 536/25.6 |
| 5,612,199 A | 3/1997 | Western et al. | 435/91.1 |
| 5,700,637 A | 12/1997 | Southern | 435/6 |
| 5,750,341 A | 5/1998 | Macevicz | 435/6 |
| 5,919,523 A | 7/1999 | Sundberg et al. | 427/333 |
| 5,959,463 A | 9/1999 | Funakura et al. | 324/765 |
| 6,124,090 A | 9/2000 | Rose et al. | 435/6 |
| 6,136,962 A | 10/2000 | Shi et al. | 536/23.1 |
| 6,261,797 B1 | 7/2001 | Sorge et al. | 435/41 |
| 6,294,323 B1 | 9/2001 | Ullman et al. | 435/6 |
| 6,306,597 B1 | 10/2001 | Macevicz | 435/6 |
| 6,365,375 B1 | 4/2002 | Dietmaier et al. | 435/91.1 |
| 6,375,903 B1 | 4/2002 | Cerrina et al. | 422/131 |
| 6,391,544 B1 | 5/2002 | Salituro et al. | 435/6 |
| 6,800,439 B1 | 10/2004 | McGall et al. | 435/6 |
| 6,824,866 B1 | 11/2004 | Glazer et al. | 428/317.9 |
| 6,830,890 B2 | 12/2004 | Lockhart et al. | 435/6 |
| 6,833,450 B1 | 12/2004 | McGall et al. | 536/25.3 |
| 2002/0081582 A1 | 6/2002 | Gao et al. | 435/6 |
| 2003/0068633 A1 | 4/2003 | Belshaw et al. | 435/6 |
| 2003/0108867 A1 | 6/2003 | Chee et al. | 435/6 |

FOREIGN PATENT DOCUMENTS

| | | |
|---|---|---|
| EP | 1 256 632 | 11/2002 |
| WO | WO 02/24597 | 3/2002 |
| WO | WO 03/040410 | 5/2003 |
| WO | WO 03/046223 | 6/2003 |
| WO | EO 03/065038 | 8/2003 |
| WO | WO 03/064026 | 8/2003 |
| WO | WO 03/064027 | 8/2003 |
| WO | WO 03/064699 | 8/2003 |
| WO | WO 03/066212 | 8/2003 |
| WO | WO 03/100012 | 12/2003 |
| WO | WO 2004/029586 | 4/2004 |
| WO | WO 2004/031351 | 4/2004 |
| WO | WO 2004/031399 | 4/2004 |

OTHER PUBLICATIONS

Aach and Church, "Mathematical models of diffusion-constrained polymerase chain reactions: . . .," *J. Theor. Biol.*, 228:31-46 (2004).
Alberts et al., "Macromolecules: Structure, Shapes and Information," *Molecular Biology of the Cell*, Chapter 3, pp. 88-91, 3d edition, Garland Publishing (1994).
Albretsen et al., "Applications of magnetic Beads with Covalently Attached Oligonucleotides . . . ," *Anal. Biochem.* 189:40-50 (1990).
Blanchard, "Synthetic DNA Arrays," *Genetic Engineering*, vol. 20:111-123, Plenum Press (1998).
Brenner et al., "Gene expression analysis by massively parallel signature sequencing (MPSS) on microbead arrays," *Nat. Biotech.* 18:630-634 (2000).
Butz et al., "Characterization of mutations and loss of heterozygosity of pt3 . . . ," *BMC Biotechnol.* 3:11-16 (2003).
Carrell et al., "A Novel Procedure for the Synthesis of Libraries Containing Small Organic Molecules," *Angew. Chem. Int. Ed. Engl.*, 33:2059-2061 (1994).
Carrell et al., "A Solution-Phase Screening Procedure for the Isolation of Active Compounds from a Library of Molecules," *Angew. Chem. Int. Ed. Engl.*, 33:2061-2065 (1994).
Cho et al., "An Unnatural Biopolymer," *Science* 261:1303-1305 (1993).
Denkov et al., "Mechanism of Formulation of Two-Dimensional Crystals from Latex Particles on Substrates," *Langmuir* 8:3183-3190 (1992).
DeWitt et al., "'Diversonmers': An Approach to nonpeptide, nonligomeric chemical diversity," *Proc. Natl. Acad. Sci. USA*, 90:6909-6913 (1993).
Dressman et al., "Transforming signle DNA molecules into fluorecent magnetic particles for detection adn enumeration of genetic variations," *Proc. Natl. Acad. Sci.* USA, 100(15):8817-8822 (2003).

(Continued)

*Primary Examiner*—James Martinell
(74) *Attorney, Agent, or Firm*—Banner & Witcoff, Ltd.

(57) ABSTRACT

Miniaturized, high-density, bead-based arrays are provided. Methods of producing and using clonal beads and producing and using miniaturized, high density, bead-based arrays are also provided.

53 Claims, 16 Drawing Sheets
(8 of 16 Drawing Sheet(s) Filed in Color)

OTHER PUBLICATIONS

Duggan et al., "Expression profiling using cDNA microarrays," *Nature Genetics Supplement*, S21:10-14 (1999).

Duncan et al., "Affinity Chromatography of a Sequence-Specific DNA Binding Protein," *Anal. Biochem.* 169:104-108 (1988).

Erb et al., "Recursive deconvolution of combinatorial chemical libraries," Proc. Natl. Acad. Sci. USA, 91:114122-11426 (1994).

Fitzgerald et al., "Rapid shotgun cloning utilizing the two base recognition endonuclease CviJI," *Nucleic Acids Res.*, 20:3753-3762 (1992).

Gallop et al., "Applications of Combinatorial Technologies to Drug Discovery, . . . ," J. Med. Chem.,37(9):1233-1251 (1994).

Guatelli et al., "Isothermal, in vitro amplification of nucleic acids by a multienzyme reaction modeled after retroviral replication," Proc. Natl. Acad. Sci U.S.A., 87:1874-1878 (1990).

Goldkorn and Prockop, "A simple and efficient enzymatic method for covalent attachment of DNA to cellulose. . . . ," *Nucleic Acids Res.* 14:9171-9191 (1986).

Hoover et al., "DNA Works: an automated method for designing oligonucleotides for PCR-based gene synthesis," *Nucleic Acids Res.* 30(10):e43-e49 (2002).

Jaffe et al., "An Artificial Gene for Human Porpobilinogen Synthase Allows Cmparison of an allelic Variation Implicated in Susceptibility to Lead Poisoning," *J. Biol. Chem.* 275(4):2619-2626 (2000).

Kanehisa, "Use of statisical criteria for screening potential homologies in nucleic acid sequences," *Nucleic Acids*, 12:203-213 (1984).

Kwoh et al., "Transcription-based amplification system and detection of amplified human immunodeficiency virus type 1 with a bead-based sandwich hybridization format," *Proc. Natl. Acad. Sci.* U.S.A., 86:1173-1177 (1989).

Landegren et al., "A Ligase-Mediated Gene Detection Technique," *Science*, 241:1077-1080 (1988).

Langdale and Malcolm, "A rapid method of gene detection using DNA bound to Sephacryl," *Gene* 36:201-210 (1985).

Lizardi et al., "Exponential Amplification of Recombinant-RNA Hybridization Probes," *BioTechnology* 6:1197-1123 (1988).

Lund et al., "Assessment of methods for covalent binding of nucleic acids to magnetic beads . . . ," *Nucleic Acid Res.* 16(22):10861-10880 (1988).

Matsumura et al., "Gene expression analysis of plant host-pathogen interactions by SuperSAGE," *Proc. Natl. Acad. Sci.* U.S.A., 100(26):15718-15723 (2003).

Matteucci et al., "Synthesis of deoxyoligonucleotides on a polymer support," *J. Am. Chem. Soc.*, 103(11):3185-3191 (1981).

McGall et al., "Light-directed synthesis of high-density oligonucleotide arrays using semiconductor photoresists," *Proc. Natl. Acad. Sci.* U.S.A., 93:13555-135600 (1996).

Merritt et al., "Parallel competition analysis of *Saccharomyces cerevisiae* strains differing by a single base using polymerase colonies," *Nucleic Acids Res.*, 31(15):e84 8 pages (2003).

Mikkilineni et al., "Digital Quantitavie Measurements of Gene Expression," *Biotechnol. Bioeng.*, 86(2):117-124 (2003).

Mita et al., "Fluorescent in situ sequencing on polymerase colonies," *Anal. Biochem.*, 320(1):55-65 (2003).

Mitra et al., "Digital genotyping and haplotyping with polymerase colonies," *Proc. Natl. Acad. Sci.* USA 100(10):5926-5931 (2003).

Nakazawa et al., "UV and skin cancer: . . . ," *Proc. Natl. Acad. Sci.* U.S.A. 91:360-364 (1994).

Polsky-Cynkin et al., "Use of DNA Immobilized on Plastic and Agarose Supports to Detect DNA by Sandwich Hybridization," *Clin. Chem.*,31:1438-1433 (1985).

Ranki et al., "Sandwich hybridization as a convenient method for the detection of nucleic acids in crude samples," *Gene*, 21:77-85 (1983).

Ronaghi et al., "A Sequencing Method Based on Real-Time Pyrophsphate," *Science* 281:363-365 (1998).

Rouillard et al., "Gene2Oligo: oligonucleotide design for in vitro gene synthesis," *Bucleic Acids Res.* 32:W176-W180 (2004).

Saha et al., "Using the transcriptome to annotate the genome," *Nat. Biotechnol.* 20:508-511 (2002).

Shendure et al., "Advanced Sequencing Technologies . . . ," *Nat. Rev.*, 5:335-344 (2004).

Shi et al., "Expressed CpG Island Sequence Tag Microarray for Dual Screening of DNA Hypermethylation and Gene Silencing in Cancer Cells," *Cancer Res.*, 62:3214-3220 (2002).

Shiraki et al., "Cap analysis gene expression for high-throughput analysis of transcriptional starting point and identification of promoter usage," *Proc. Natl. Acad. Sci.* U.S.A., 100(26):15776-15781 (2003).

Ueki et al., "Identification and Characterization of Differentially Methylated CpG Islands in Pancreatic Carcinoma," *Cancer Res.*, 61:8540-8546 (2001).

Van Ness et al., "A versatile solid support system for oligodeoxynucleotide probe-based hybridization assays," *Nucleic Acids Res.* 19(12):3345-3350 (1991).

Velculescu et al., "Serial Analysis of Gene Expression," *Science*, 5235:484-487 (1995).

Williams et al., "In Vivo Protein Cyclization Promoted by a Circularly Permuted *Synechocystis* sp. PCC6803 DnaB Mini-intein," *J. Biol. Chem.* 277(10):7790-7798 (2002).

Wolf et al., "Rapid hybridization kinetics of DNA attached to submicron latex particles," *Nucleic Acids Res.*, 15(7):2911-2926 (1987).

Yan et al., "CpG Island Arrays: . . . ," *Clin. Cancer Res.*, 6:1432-1438 (2000).

Zhu et al., "Single Molecule Profiling of Alternative Pre-mRNA Splicing," *Science*, 301 (5634):836-838 (2003).

Zuckermann et al., "Discovery of Nanomolar Ligands for 7-Transmembrane G-Protein-Coupled Receptors from a Divers N-(Subsituted)glycine Peptoid Library," J. Med. Chem. 37:2678-2685 (1994).

*Current Protocols in Molecular Biology*, John Wiley & Sons, N.Y., pp. 6.3.1-6.3.6 (1989).

*Microarrays: Making Them and Using Them* In Microarray Bioinformatics, Cambridge University Press, 2003, pp. 1-10.

Mitra and Church, "*In situ* localized amplification and contact replication of many individual DNA molecules," *Nucl. Acids Res.* ,27(24):e34, pages i through vi (1999).

Shendure et al., "Accurate Multiplex Polony Sequencing of an Evolved Bacterial Genome," *Science*, 309:1728-1732 (2005).

A

B

A B

C D

US 7,425,431 B2

POLONY FLUORESCENT IN SITU SEQUENCING BEADS

RELATED APPLICATIONS

This application claims priority from PCT Application No. PCT/US05/06425, filed Feb. 28, 2005, which designated the United States; and from U.S. Provisional Patent Application No. 60/548,631 filed on Feb. 27, 2004, both of which are hereby incorporated by reference in their entirety for all purposes.

STATEMENT OF GOVERNMENT INTERESTS

This invention was made with Government support under grant number F30602-01-2-0586 awarded by DARPA and grant number DE-FG02-02ER63445 awarded by the Department of Energy. The Government has certain rights in the invention.

FIELD OF THE INVENTION

The present invention relates to miniaturized, high density, bead-based arrays, methods of producing and using miniaturized, high density, bead-based arrays and methods of producing and using the components thereof.

BACKGROUND OF THE INVENTION

Polymerase colony (polony) technology is a single-molecule amplification technology which allows the sequence of each individual molecule to be elucidated in a highly parallel manner. However, the throughput of polony technology is inversely proportional to the size of individual colonies, which ranges from tens to thousands of microns.

Methods for generating populations of clonal microspheres (i.e., beads bearing clonally amplified DNA) are known in the art (e.g., Dressman (2003) *Proc. Natl. Acad. Sci. USA* 100:8817; Brenner et al. (2000) *Nat. Biotech.* 18:630). However, these methods suffer from several drawbacks. In Dressman et al., beads are analyzed via fluorescence activated cell sorting (FACS), which is expensive to operate and suffers too low of a throughput (i.e., less than 70,000 events per second) to process hundreds of millions of beads. In Brenner et al., beads are manipulated to form a packed, planar array, such that the physical packing limits scattering of the beads.

SUMMARY

The present invention is based in part on the discovery of a novel method for the efficient, cost-effective production of bead-based arrays. Such arrays are particularly useful for genetics research and diagnostic applications. The methods and compositions described herein allow for tens of millions to billions of discrete nucleic acid sequences to be queried in a reasonable time in an economical manner.

Embodiments of the present invention are directed to bead-based arrays and methods of making bead-based arrays. In accordance with certain embodiments, arrays having a plurality of beads wherein an individual bead has a population of substantially identical nucleic acid sequences attached to them and wherein the population of substantially identical nucleic acid sequences differs in sequence from the population of substantially identical nucleic acid sequences attached to other beads are provided. The plurality of beads is immobilized in a semi-solid medium to form an array. The semi-solid medium can be made from polyacrylamide, cellulose, polyamide, cross-linked agarose, cross-linked dextran or cross-linked polyethylene glycol. In certain aspects, the semi-solid medium has x, y and z axes, and the plurality of beads is randomly arranged relative to the x and y axes. The beads can be immobilized as a monolayer, for example, near the top surface of the semi-solid medium.

In certain aspects, the semi-solid medium can be attached to a solid support such as a microscope slide or a flow cell. The solid support can be attached to the bottom surface of the semi-solid medium.

In other aspects, two, three or four different populations of substantially identical nucleic acid sequences can be attached to the beads. In other aspects, the beads are clonal beads. In still other aspects, the beads include a library.

In other embodiments, methods of making bead-based arrays including providing a plurality of beads having a population of substantially identical nucleic acid sequences attached, immobilizing the beads in a semi-solid medium to form an array, and amplifying the population of substantially identical nucleic acid sequences to form a plurality of beads having an amplified population of substantially identical nucleic acid sequences attached are provided. In certain aspects, the semi-solid medium includes an amplification primer. In other aspects, the semi-solid medium includes an additive that forms voids in the semi-solid medium, such as a cationic lipid, polyamine or polycation.

In other embodiments, methods of making bead-based arrays including providing a plurality of beads having a population of substantially identical nucleic acid sequences attached, and amplifying the population of substantially identical nucleic acid sequences to form a plurality of immobilized beads having an amplified population of substantially identical nucleic acid sequences attached are provided. The beads are then immobilized in a semi-solid medium to form an array. In certain aspects, amplifying is performed by emulsion PCR.

In still other embodiments, methods of making bead-based arrays including providing a plurality of beads having a population of substantially identical nucleic acid sequences attached, and amplifying the population of substantially identical nucleic acid sequences to form a plurality of beads having an amplified population of substantially identical nucleic acid sequences attached are provided. The plurality of beads having an amplified population of substantially identical nucleic acid sequences attached thereto is enriched to form an enriched population of beads, and the beads are immobilized in a semi-solid medium to form an array.

Embodiments of the present invention are directed to methods for enriching a population of beads having a first nucleic acid sequence attached. These methods include providing a population of beads wherein at least a portion of the population includes a bead having a first nucleic acid sequence attached. The population of beads is contacted with a second nucleic acid sequence that is complementary to the first nucleic acid sequence, and the population of beads and the second nucleic acid sequence are incubated together such that hybridization occurs to form a population of hybridized beads and a population of unhybridized beads. The population of hybridized beads is then separated from the population unhybridized beads. In certain aspects, the second nucleic acid is immobilized on a capture bead. In other aspects, the population of hybridized beads are separated from the population of unhybridized beads by density or affinity.

In accordance with another embodiment, kits are provided containing an array having a plurality of beads immobilized in a semi-solid medium, in which a population of substantially identical nucleic acid sequences are attached to the beads.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing and other features and advantages of the present invention will be more fully understood from the following detailed description of illustrative embodiments taken in conjunction with the accompanying drawings.

DETAILED DESCRIPTION

Figure 1:
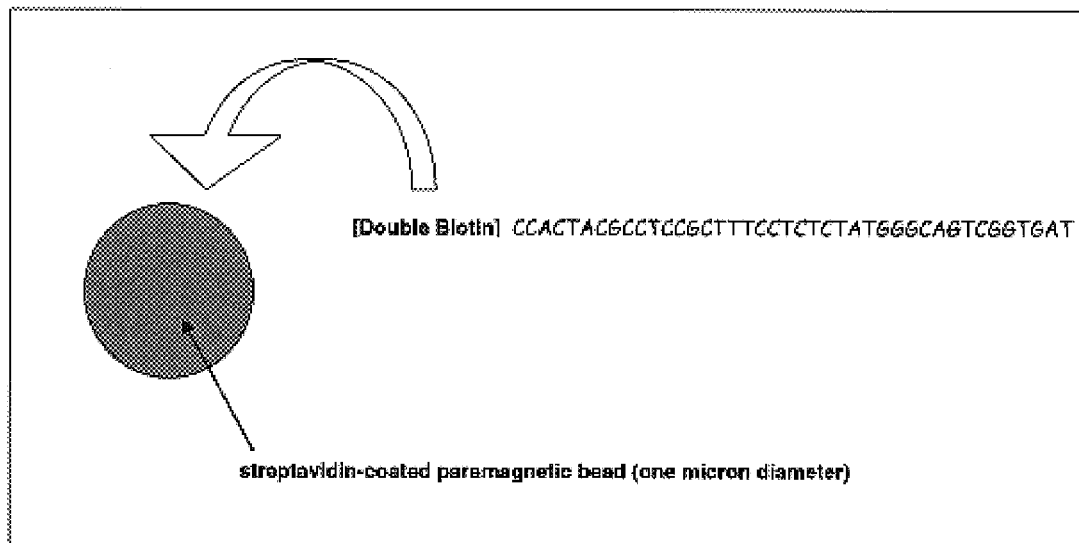
FIG. 1 depicts a schematic of a biotinylated primer (SEQ ID NO: 1) and a streptavidin coated bead.

The present invention provides methods of preparing and arraying large numbers of microspheres bearing amplified DNA. A variety of hybridization and enzymatic-based methods can then be applied to the amplified DNA the beads of the array simultaneously using a single small reagent volume. In certain aspects, parallel nucleic acid analysis, e.g., DNA sequencing and RNA expression profiling, may be combined with the beads of the invention. The beads and methods of making and using bead-based, high-density arrays described herein are useful for a variety of genetics-based research and diagnostic applications, which are discussed further below.

The present invention provides advantages over bead-based methods known in the art. For example, methods described herein greatly increase resolution of current methods of sequencing by decreasing readout to the scale of a single micron. Another advantage of certain methods of the invention is that imbedding beads in a polymer or gel enhances current methods of "polymerase-trapping." Yet another advantage of certain of the methods described herein is that imbedding can aid image registration since the beads stay immobilized with better than 0.4 micron precision. The present invention also advantageously provides a facile method for enriching amplified beads relative to unamplified beads. In other aspects of the invention, immobilized beads comprising a monolayer are ordered with respect to the Z axis, but are entirely disordered with respect to the X and Y axes. This provides the benefit of allowing one to generate bead arrays without the need for using a substrate that generates order in the bead pattern (e.g., a surface with etched wells for beads to fall into). A further advantage of methods described herein for embedding or otherwise attaching a bead is that it allows for integration into an acquisition system in which the beads are moved relative to the detecting means to allow for collection of data from a larger element than could typically be used with the detecting means.

The present invention provides beads and bead-based arrays. As used herein, the term "bead" refers to a discrete particle that may be spherical (e.g., microspheres) or have an irregular shape. Beads may be as small as approximately 0.1 µm in diameter or as large approximately several millimeters in diameter. Beads typically range in size from approximately 0.1 µm to 200 µm in diameter, from approximately 0.25 µm to 100 µm in diameter, from approximately 0.5 µm to 50 µm in diameter, from approximately 0.6 µm to 40 µm in diameter, from approximately 0.7 µm to 30 µm in diameter, from approximately 0.8 µm to 20 µm in diameter, from approximately 0.9 µm to 10 µm in diameter or from approximately 1 µm to 9 µm in diameter. In certain aspects, beads of the invention are approximately 1 µm, 2 µm, 3 µm, 4 µm, 5 µm, 6 µm, 7 µm, 8 µm or 9 µm in diameter. Beads may comprise a variety of materials including, but not limited to, paramagnetic materials, ceramic, plastic, glass, polystyrene, methylstyrene, acrylic polymers, titanium, latex, sepharose, cellulose, nylon and the like.

In accordance with certain examples, beads may have functional groups on their surface which can be used to bind nucleic acid sequences to the bead. Nucleic acid sequences can be attached to a bead by hybridization (e.g., binding to a polymer), covalent attachment, magnetic attachment, affinity attachment and the like. For example, the bead can be coated with streptavidin and the nucleic acid sequence can include a biotin moiety. The biotin is capable of binding streptavidin on the bead, thus attaching the nucleic acid sequence to the bead. Beads coated with streptavidin, oligo-dT, and histidine tag binding substrate are commercially available (Dynal Biotech, Brown Deer, Wis.). Beads may also be functionalized using, for example, solid-phase chemistries known in the art, such as those for generating nucleic acid arrays, such as carboxyl, amino, and hydroxyl groups, or functionalized silicon compounds (see, for example, U.S. Pat. No. 5,919,523, incorporated herein by reference in its entirety for all purposes).

Methods of immobilizing oligonucleotides to a support are described are known in the art (beads: Dressman et al. (2003) *Proc. Natl. Acad. Sci. USA* 100:8817, Brenner et al. (2000) *Nat. Biotech.* 18:630, Albretsen et al. (1990) *Anal. Biochem.* 189:40, and Lang et al. *Nucleic Acids Res.* (1988) 16:10861; nitrocellulose: Ranki et al. (1983) *Gene* 21:77; cellulose: (Goldkorn (1986) *Nucleic Acids Res.* 14:9171; polystyrene: Ruth et al. (1987) Conference of Therapeutic and Diagnostic Applications of Synthetic Nucleic Acids, Cambridge U.K.; teflon-acrylamide: Duncan et al. (1988) *Anal. Biochem.* 169: 104; polypropylene: Polsky-Cynkin et al. (1985) *Clin. Chem.* 31:1438; nylon: Van Ness et al. (1991) *Nucleic Acids Res.* 19:3345; agarose: Polsky-Cynkin et al., *Clin. Chem.* (1985) 31:1438; and sephacryl: Langdale et al. (1985) *Gene* 36:201; latex: Wolf et al. (1987) *Nucleic Acids Res.* 15:2911; incorporated by reference herein in their entirety for all purposes) and are described further herein.

As used herein, the term "attach" refers to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in *Molecular Biology of the Cell*, 3d edition, Garland Publishing, 1994, incorporated herein by reference in its entirety for all purposes.

Embodiments of the present invention provide a bead upon which one to millions of copies of a nucleic acid sequence (e.g., an oligonucleotide sequence or a polynucleotide sequence) is attached. In one aspect, the bead can have multiple copies of a single nucleic acid sequence attached thereto (i.e., clonal beads). In another aspect, the bead may have two, three, four, five, ten or more species of nucleic acid sequences attached thereto. For example, in one aspect, both orientations of a genetic sequence (i.e., the positive and the negative strands) may be attached to a bead.

In certain embodiments, beads are provided that have a population of substantially identical nucleic acid sequences attached thereto. As used herein, the term "substantially identical nucleic acid sequence" is intended to include, but is not limited to, nucleic acid sequences having at least 50%, 55%, 60%, 65%, 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% sequence identity to one another. In certain aspects, substantially identical includes 100% sequence identity. The term substantially identical to may apply to all nucleic acid sequences attached to a bead, to primers attached to a bead and/or to amplification products attached to a bead.

As used herein, the term "oligonucleotide" is intended to include, but is not limited to, a single-stranded DNA or RNA molecule, typically prepared by synthetic means. Nucleotides of the present invention will typically be the naturally-occurring nucleotides such as nucleotides derived from adenosine, guanosine, uridine, cytidine and thymidine. When oligonucleotides are referred to as "double-stranded," it is understood by those of skill in the art that a pair of oligonucleotides exists in a hydrogen-bonded, helical array typically associated with, for example, DNA. In addition to the 100% complementary form of double-stranded oligonucleotides, the term "double-stranded" as used herein is also meant to include those form which include such structural features as bulges and loops (see Stryer, *Biochemistry*, Third Ed. (1988), incorporated herein by reference in its entirety for all purposes). As used herein, the term "polynucleotide" refers to a strand of nucleic acids that can be a variety of different sizes. Polynucleotides may be the same size as an oligonucleotide, or may be two-times, three-times, four-times, five-times, ten-times, or greater than the size of an oligonucleotide. Oligonucleotides and polynucleotides include those attached to beads and made by amplification (i.e., "amplification products") using any of the methods described herein.

Oligonucleotides and/or polynucleotides may be isolated from natural sources or purchased from commercial sources. Oligonucleotide and/or polynucleotide sequences may be prepared by any suitable method, e.g., the phosphoramidite method described by Beaucage and Carruthers ((1981) *Tetrahedron Lett.* 22: 1859) or the triester method according to Matteucci et al. (1981) *J Am. Chem. Soc.* 103:3185), both incorporated herein by reference in their entirety for all purposes, or by other chemical methods using either a commercial automated oligonucleotide synthesizer or high-throughput, high-density array methods described herein and known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides may also be obtained commercially from a variety of vendors.

In certain embodiments of the invention oligonucleotides and/or polynucleotides may be prepared using a variety of microarray technologies known in the art. Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) Proc. *Natl. Acad. Sci. U.S.A.* 93:13555; *Synthetic DNA Arrays* In Genetic Engineering, Vol. 20:111, Plenum Press (1998); Duggan et al. (1999) *Nat. Genet.* S21:10; *Microarrays: Making Them and Using Them* In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Application Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597; incorporated herein by reference in their entirety for all purposes.

In certain embodiments, the beads of the invention are useful for analyzing libraries, e.g., genomic libraries, cDNA libraries and the like. Examples of methods for the synthesis of molecular libraries can be found in the art, for example in:

DeWitt et al. (1993) *Proc. Natl. Acad Sci. USA* 90:6909; Erb et al. (1994) *Proc. Natl. Acad. Sci. USA* 91:11422; Zuckermann et al. (1994) *J Med Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J Med. Chem.* 37:1233, incorporated herein by reference in their entirety for all purposes. Libraries are described further herein.

In certain embodiments, the beads of the invention are immobilized in a semi-solid medium. Semi-solid media comprise both organic and inorganic substances, and include, but are not limited to, polyacrylamide, cellulose and polyamide (nylon), as well as cross-linked agarose, dextran or polyethylene glycol. For example, beads described herein can be physically immobilized in a polymer gel. The gel can be larger in its X and Y dimensions (e.g., several centimeters) than its Z-dimension (e.g., approximately 30 microns), wherein the Z-dimension is substantially thicker than the beads that are immobilized within it (e.g., 30 micron gel versus one micron beads).

In certain aspects, at least about 5%, 10%, 15%, 20%, 25%, 30%, 35%, 40%, 45%, 50%, 55%, 60%, 65%, 75%, 80%, 85%, 90%, 91%, 92%, 93%, 94%, 95%, 96%, 97%, 98%, 99% or more of the beads immobilized in a semi-solid medium have nucleic acid sequences (e.g., amplified nucleic acid sequences) attached thereto. That is, some of the beads immobilized in the semi-solid medium can be empty (i.e., do not have nucleic acid sequences attached thereto), some can have only amplification primer (i.e., do not have amplified nucleic acid sequences attached thereto) and/or some can have a heterogeneous population of nucleic acids (i.e., not substantially identical sequences) attached thereto.

In other aspects, each immobilized bead that contains a nucleic acid sequences attached thereto will have different nucleic acid sequences than the other immobilized beads. That is, 50%, 45%, 40%, 35%, 30%, 25%, 20%, 15%, 14%, 13%, 12%, 11%, 10%, 9%, 8%, 7%, 6%, 5%, 4%, 3%, 2%, 1% or less of the immobilized beads will have nucleic acid sequences (e.g., amplified nucleic acid sequences) attached thereto that are substantially identical to the nucleic acid sequences attached to one or more of the other immobilized beads. Nucleic acid sequences attached to a bead may apply to all nucleic acid sequences attached to a bead, to primers attached to a bead and/or to amplification products attached to a bead.

In still other aspects, a semi-solid medium of the invention is used in conjunction with a solid support. For example the gel described in the paragraph above can be polymerized in such a way that one surface of the gel is attached to a solid support (e.g., a glass surface), while the other surface of the gel is exposed. In certain aspects, the gel can be poured in such a way that the beads form a monolayer that resides near the exposed surface of the gel.

Solid supports of the invention may be fashioned into a variety of shapes. In certain embodiments, the solid support is substantially planar. Examples of solid supports include plates such as slides, microtitre plates, flow cells, coverslips, microchips, and the like, containers such as microfuge tubes, test tubes and the like, tubing, sheets, pads, films and the like. Additionally, the solid supports may be, for example, biological, nonbiological, organic, inorganic, or a combination thereof. In certain embodiments, beads and/or the solid supports may be functionalized such that the beads may be bound to the solid support. Functional groups are discussed further herein.

In certain embodiments, an array of beads can be imaged on a standard epifluorescence microscope. The use of immobilized beads allows the array to be subjected to multiple cycles of hybridization/enzymatic-based manipulations followed by imaging of visually detectable labels on molecules hybridized to the DNA immobilized on the beads or visually detectable labels incorporated into the bead-immobilized DNA itself. A variety of detectable labels can be used with the sequencing assays described further herein. Examples of labels for use in the present invention include visually detectable labels such as fluorescein (e.g., FITC), rhodamine (e.g., TRITC, RITC), DAPI, BODIPY, Cy3, Cy5, Alexa, Texas red, Cascade blue, green fluorescent protein (GFP), yellow fluorescent protein (YFP), cyan fluorescent protein (CFP), horseradish peroxidase, alkaline phosphatase, avidin, biotin, luciferase (e.g., *renilla* luciferase, firefly luciferase), and the like. Many suitable labels are known in the art and can be ordered, for example, from the catalogs from Molecular Probes (Eugene, Oreg.) and Sigma-Aldrich (St. Louis, Mo.), incorporated herein by reference in their entirety for all purposes.

Embodiments of the present invention are further directed to the amplification of nucleic acid sequences on beads. In certain aspects, methods of amplifying oligonucleotides include emulsion PCR, which is described further below. Other methods of amplifying nucleic acid sequences include, but are not limited to, rolling circle amplification (hyperbranched or linear) in emulsions using beads with primers to capture reaction products; rolling circle amplification (hyperbranched or linear) in aqueous solution, followed by clonal 'capture' on beads; helicase displacement amplification (HDA) in emulsions; and rolling circle amplification in situ using, for example, $SiO_2$-surface oligos, or a thin gel-immobilized oligo layer.

In certain aspects, methods of amplifying oligonucleotides involves the use of PCR, such as anchor PCR or RACE PCR, or, alternatively, in a ligation chain reaction (LCR) (see, e.g., Landegran et al. (1988) *Science* 241:1077-1080; and Nakazawa et al. (1994) *Proc. Natl. Acad Sci. USA.* 91:360-364; incorporated herein by reference in their entirety for all purposes). Alternative amplification methods include: self sustained sequence replication (Guatelli et al. (1990) *Proc. Natl. Acad. Sci. USA* 87:1874, incorporated herein by reference in its entirety for all purposes), transcriptional amplification system (Kwoh et al. (1989) *Proc. Natl. Acad Sci. US.* 86:1173, incorporated herein by reference in its entirety for all purposes), Q-Beta Replicase (Lizardi et al. (1988) *Bio-Technology* 6:1197, incorporated herein by reference in its entirety for all purposes), recursive PCR (Jaffe et al. (2000) *J Biol. Chem.* 275:2619; and Williams et al. (2002) *J Biol. Chem.* 277:7790; incorporated herein by reference in their entirety for all purposes) or any other nucleic acid amplification method using techniques well known to those of skill in the art. A variety of amplification methods are described in U.S. Pat. Nos. 6,391,544, 6,365,375, 6,294,323, 6,261,797, 6,124,090 and 5,612,199, incorporated herein by reference in their entirety for all purposes.

Embodiments of the present invention are directed to methods of amplifying oligonucleotides using the amplification methods described herein. In certain aspects, oligonucleotides are amplified by selectively hybridizing an amplification primer to an amplification site at the 3' end of an oligonucleotide using conventional methods. Amplification primers are 6 to 100, and even up to 1,000, nucleotides in length, but typically from 10 to 40 nucleotides, although oligonucleotides of different length are of use. Amplification primers may be present in solution, such as with emulsion PCR, and/or present in the semi-solid media described herein.

Typically, selective hybridization occurs when two nucleic acid sequences are substantially complementary, i.e., at least about 65% 75%, 80%, 85%, 90%, 91%, 92%, 93%, 94%, 95%, 96%, 97%, 98% 99%, 99.1%, 99.2%, 99.3%, 99.4%, 99.5%, 99.6%, 99.7%, 99.8%, 99.9% or 100% complementary over a stretch of at least 14 to 25 nucleotides. See Kanehisa, M., 1984, *Nucleic Acids Res.* 12: 203, incorporated herein by reference in its entirety for all purposes.

Overall, five factors influence the efficiency and selectivity of hybridization of the primer to a second nucleic acid molecule. These factors, which are (i) primer length, (ii) the nucleotide sequence and/or composition, (iii) hybridization temperature, (iv) buffer chemistry and (v) the potential for steric hindrance in the region to which the primer is required to hybridize, are important considerations when non-random priming sequences are designed.

There is a positive correlation between primer length and both the efficiency and accuracy with which a primer will anneal to a target sequence; longer sequences have a higher $T_m$ than do shorter ones, and are less likely to be repeated within a given target sequence, thereby cutting down on promiscuous hybridization. Primer sequences with a high G-C content or that comprise palindromic sequences tend to self-hybridize, as do their intended target sites, since unimolecular, rather than bimolecular, hybridization kinetics are generally favored in solution; at the same time, it is important to design a primer containing sufficient numbers of G-C nucleotide pairings to bind the target sequence tightly, since each such pair is bound by three hydrogen bonds, rather than the two that are found when A and T bases pair. Hybridization temperature varies inversely with primer annealing efficiency, as does the concentration of organic solvents, e.g., formamide, that might be included in a hybridization mixture, while increases in salt concentration facilitate binding. Under stringent hybridization conditions, longer probes hybridize more efficiently than do shorter ones, which are sufficient under more permissive conditions. Stringent hybridization conditions typically include salt concentrations of less than about 1M, more usually less than about 500 mM and preferably less than about 200 mM. Hybridization temperatures range from as low as 0° C. to greater than 22° C, greater than about 30° C., and (most often) in excess of about 37° C. Longer fragments may require higher hybridization temperatures for specific hybridization. As several factors affect the stringency of hybridization, the combination of parameters is more important than the absolute measure of any one alone. Hybridization conditions are known to those skilled in the art and can be found in *Current Protocols in Molecular Biology*, John Wiley & Sons, N.Y. (1989), 6.3.1-6.3.6, incorporated herein by reference in its entirety for all purposes.

Primers are designed with the above first four considerations in mind. While estimates of the relative merits of numerous sequences are made mentally, computer programs have been designed to assist in the evaluation of these several parameters and the optimization of primer sequences (see, e.g., Hoover et al. (2002) *Nucleic Acids Res.* 30:e43, and Rouillard et al. (2004) *Nucleic Acids Res.* 32:W176, incorporated by reference herein in their entirety for all purposes).

In accordance with certain examples, methods for enriching beads having a nucleic acid sequence of interest attached thereto are provided. Beads having a nucleic acid sequence of interest may be enriched by contacting a population of beads (wherein at least one of the beads has a nucleic acid sequence of interest attached thereto) with a nucleic acid sequence complementary to the nucleic acid sequence of interest (i.e., a complementary nucleic acid sequence) under conditions that allow hybridization of the nucleic acid sequence of interest and the complementary nucleic acid sequence. The unhybridized beads are then separated from the hybridized beads which contain the nucleic acid sequence of interest attached thereto using methods known in the art. In certain aspects, beads having a nucleic acid sequence of interest attached thereto are enriched at least about 5%, 10%, 15%, 20%, 25%, 30%, 35%, 40%, 45%, 50%, 55%, 60%, 65%, 75%, 80%, 85%, 90%, 91%, 92%, 93%, 94%, 95%, 96%, 97%, 98%, 99% or more over the percentage of beads having a nucleic acid sequence of interest attached thereto in the starting population of beads. In certain embodiments, the complementary nucleic sequence is immobilized on a support. Suitable supports include, but are not limited to, synthetic polymer supports, e.g., polystyrene, polypropylene, substituted polystyrene (e.g., aminated or carboxylated polystyrene), polyacrylamides, polyamides, polyvinylchloride, and the like, polymeric beads, magnetic beads, glass beads, sepharose, agarose, cellulose, or any material useful in affinity chromatography. Methods of enriching beads having a nucleic acid sequence of interest are described further herein.

In accordance with certain examples, methods of sequencing nucleic acid sequences on beads are provided. General sequencing methods known in the art, such as sequencing by extension with reversible terminators, fluorescent in situ sequencing (FISSEQ), pyrosequencing, massively parallel signature sequencing (MPSS) and the like (described in Shendure et al. (2004) *Nat. Rev.* 5:335, incorporated herein by reference in its entirety), are suitable for use with the beads and bead-based arrays described herein. Reversible termination methods us step-wise sequencing-by-synthesis biochemistry that coupled with reversible termination and removable fluorescence (Shendure et al. supra ands U.S. Pat. Nos. 5,750,341 and 6,306,597, incorporated herein by reference. FISSEQ is a method whereby DNA is extended by adding a single type of fluorescently-labelled nucleotide triphosphate to the reaction, washing away unincorporated nucleotide, detecting incorporation of the nucleotide by measuring fluorescence, and repeating the cycle. At each cycle, the fluorescence from previous cycles is bleached or digitally subtracted or the fluorophore is cleaved from the nucleotide and washed away. FISSEQ is described further in Mitra et al. (2003) *Anal. Biochem.* 320:55, incorporated herein by reference in its entirety for all purposes. Pyrosequencing is a method in which the pyrophosphate (PPi) released during each nucleotide incorporation event (i.e., when a nucleotide is added to a growing polynucleotide sequence). The PPi released in the DNA polymerase-catalyzed reaction is detected by ATP sulfurylase and luciferase in a coupled reaction which can be visibly detected. The added nucleotides are continuously degraded by a nucleotide-degrading enzyme. After the first added nucleotide has been degraded, the next nucleotide can be added. As this procedure is repeated, longer stretches of the template sequence are deduced. Pyrosequencing is described further in Ronaghi et al. (1998) *Science* 281:363, incorporated herein by reference in its entirety for all purposes. MPSS utilizes ligation-based DNA sequencing simultaneously on microbeads. A mixture of labelled adaptors comprising all possible overhangs is annealed to a target sequence of four nucleotides. The label is detected upon successful ligation of an adaptor. A restriction enzyme is then used to cleave the DNA template to expose the next four bases. MPSS is described further in Brenner et al. (2000) *Nat. Biotech.* 18:630, incorporated herein by reference in its entirety for all purposes.

This invention is further illustrated by the following examples, which should not be construed as limiting. The contents of all references, patents and published patent applications cited throughout this application are hereby incorporated by reference in their entirety for all purposes.

EXAMPLE I

Clonal Beads

Step 1: Coupling Oligonucleotides to Beads

Commercially available oligonucleotides obtained from Integrated DNA Technologies were used (Coralville, Iowa). The oligonucleotides were attached to streptavidin-coated paramagnetic beads (1 µM MYONE™ beads (Dynal Biotech, Brown Deer, Wis.)) via the double-biotin moieties at their 5' ends (FIG. 1). The sequence of the oligonucleotide was identical to the PR1-F section of the library molecules described in the library generation protocol below (Example VI). Subsequent to this step, this allows the bead-immobilized oligonucleotide to act as a PCR primer during amplification of a template library as described herein. In the protocols described herein, this sequence is referred to as the 'forward' PCR primer.

Steps for generating forward-primer-loaded beads were as follows:
1) Using a magnetic field to the pull beads to the side of a microcentrifuge tube, $1 \times 10^9$ MYONE™ Streptavidin paramagnetic beads (100 µL of stock solution) were washed once in 200µl TE.
2) The beads were resuspended in 180 µl Bind & Wash Buffer (5 mM Tris-HCl pH 7.5, 0.5 mM EDTA, 1.0M NaCl)
3) Beads were incubated for 30 minutes at 25° C. with 20 µl of 100 µM (2 nmole) 5' dual-biotinylated forward PCR primer PR1-F-2BIO: 2Bio-CCACTACGCCTCCGCTTT CCTCTCTATGGGCAGTCGGTGAT (SEQ ID NO:1)
4) Using a magnetic field to pull the beads to side of a microcentrifuge tube, the beads were washed twice with 200 µl TE.
5) The beads were resuspended in 200 µl TE ($5 \times 10^8$ beads/µl) and stored at 4° C. until used in subsequent steps.

Step 2: Preparing Microemulsions

PCR reactions in water-in-oil emulsions were performed. The use of an emulsion isolated very small volumes of the aqueous components of the emulsion from one another, consequently, the PCR reagents and products of the PCR reaction were isolated from one another over the course of the thermocyling reaction. The use of oligonucleotides immobilized to beads (e.g., beads from step 1) as one of the two PCR primers resulted in PCR products that were physically immobilized to the beads at the end of the PCR reaction. The template used for the PCR reaction consisted of a complex mixture of polynucleotides that contained two flanking 'common' regions, with an intervening sequence that varied from molecule to molecule. In this example, an *E. coli* genomic library was used. The common sequences flanking the unique region of this library are referred to herein as "PR1-F" and "PR1-R". A low concentration of template was used for the PCR, such that most aqueous compartments of the emulsion that contained a bead contained either zero or one template at the beginning of the PCR reaction. At the end of the PCR reaction, many beads were 'empty', as they were in a compartment that did not contain any template. Other beads were 'clonal', in that they contained thousands of copies of the same PCR product. The PCR product of each clonal bead differed from the PCR product of other clonal beads. Less common, but also present, were beads that were present in compartments with two or more templates. This third kind of 'non-clonal' bead contained a mixture of PCR products deriving from more than one template. Thus, the distribution of beads fell into three categories: empty, clonal and non-clonal, which could be modeled using Poisson distribution.

A. Preparation of Emulsion Oil Phase

Surprisingly, it has been discovered that the stability of the emulsion was very sensitive to the proportions of each component of the oil phase. Accordingly, extra care was taken when measuring each component to ensure minimal variability from one experiment to the next (e.g. using reverse pipetting, measuring by positive-displacement syringe and the like). The use of syringes to measure out 10% (v/v) Span 80 enabled consistent performance of the emulsion PCR.
1) 10% (v/v) Span 80 in mineral oil solution was prepared, measuring with a 10 ml or 1 ml syringe and 16 gauge needle:
   a) 9 ml light mineral oil
   b) 1 ml SPAN® 80 (Sigma-Aldrich, St. Louis, Mo.)
2) The following was added to a microcentrifuge tube by reverse pipetting:
   a) 545 µl light mineral oil (Sigma-Aldrich)
   b) 450 µl 10% SPAN® 80 in mineral oil
   c) 4 µl TWEEN® 80 (Sigma-Aldrich)
   d) 0.5 µl TRITON® X-100 (Sigma-Aldrich)
3) The solution was vortexed for 30 seconds to mix thoroughly.

B. Preparation of Emulsion Aqueous Phase

It was discovered that increasing the concentration of nucleotides to the high amount set forth below yielded more signal in the bead-gel-imaging system described herein. A concurrent increase in $MgCl_2$ concentration was also necessary to keep the ratio of nucleotides:$MgCl_2$ sufficiently close to 10:1.

The following were added to a microcentrifuge tube, and were mixed by pipetting gently: 8.0 µl 10× $MgCl_2$- PLATINUM® Taq PCR buffer (Invitrogen, Carlsbad, Calif.); 30 µl 50 mM $MgCl_2$ (18.75 mM) (Invitrogen); 11.3 µl 25 mM (each) dNTP mix (3.5 mM) (Invitrogen); 1.0 µl 2 mM unmodified reverse PCR primer PR1-R (Integrated DNA Technologies (IDT), Coralville, Iowa): CTGCCCCGGGT-TCCTCATTCTCT (SEQ ID NO:2); 0.4 µl 10 µM unmodified short forward PCR primer PR1-3LF: IDT, CCTCTC-TATGGGCA GTCGGTGAT (SEQ ID NO:3); 5 µl PR1-F forward-primer bearing 1-micron beads; 20.5 µl sterile $dH_2O$; 4.5 µl PLATINUM® Taq (Invitrogen; 5U/µl); and 0.25 µl 1 nM template DNA C. Preparation of Water-in-oil Emulsion The following emulsion preparation is for 5 µl (approximately $2.5 \times 10^9$) beads. The amount of template used generally yielded 10% amplified beads. Typically, 5-50 µl beads per slide were used in the absence of enrichment, or 50-200 µl enriched beads per slide were used. It has been discovered that the ratio of oil phase to aqueous phase affects the stability of the emulsion, and it has been determined that a ratio of 1:6 aqueous:oil resulted in consistently stable emulsions.
1) 400 µl oil phase was added to a 2 ml round-bottom cryogenic vial on a closed-loop magnetic stir plate set to 1400 RPM with a magnetic microstir bar.
2) 75 µl aqueous phase was added dropwise to the stirring oil phase.
3) The mixture was stirred for 30 minutes at 1400 RPM with a magnetic microstir bar (no. 58948-353, VWR Scientific, West Chester, Pa.) on a VWR Scientific model 565 magnetic stirrer.
4) The contents of the tube were split into 8×200 µl tubes (50 µl each)

D. Thermal Cycling

It was discovered that increasing the number of PCR cycles and increasing the extension time increased signal. Accordingly 120 PCR cycles were used with a 75 second extension phase.

Emulsions were thermo-cycled according to the following program (minutes: seconds):
a) 94° C. 2:00
b) 94° C. 0:15
c) 57° C. 0:30
d) 70° C. 1:15
e) repeat steps b)-d), 119 more times
f) 72° C. 2:00
g) 4° C. until use E. Beads were Recovered from the Emulsion The following protocol was used to recover beads from the emulsion:
1) Contents of 8×200 µl PCR tubes were pooled into a single 1.5 µl microcentrifuge tube.
2) 800 µl NX Buffer (100 mM NaCl; 1% TRITON® X-100; 10 mM Tris-HCl pH 7.5; 1 mM EDTA) was added.
3) The tube was vortexed for 30 seconds.
4) The tube was centrifuged at 11,000 RPM for 1.5 minutes.
5) Approximately 1150 µl supernatant was removed without disturbing pellet.
6) Step 2-5 were repeated two more times.
7) The remaining liquid was removed liquid using magnetic separation to pull beads to side of microcentrifuge tube.
8) The beads were washed twice with 50 µl TE.
9) The beads were resuspended in 5 µl TE.

F. Exonuclease Treatment to Remove Unextended Forward Primer from Beads

After emulsion PCR, 'amplified' beads bore both PCR product (double-stranded, with one strand immobilized to beads), and residual, unextended forward primer (single-stranded). It has been discovered that the residual, unextended forward primer could be the source of background signal in subsequent steps of nucleic acid analysis. Therefore, it was desirable to eliminate it. Exonuclease I was used to selectively digest the residual unextended primer.

1) The following was mixed:
   86 µl Beads+dH$_2$O
   10 µl 10× Exonuclease I reaction buffer (New England Biolabs, Beverly, Mass.)
   4 µl of Exonuclease I (20 units/µl, New England Biolabs)
2) The mixture was incubated at 37° C. for 1 hour, mixing once at the 30 minute time-point to disrupt bead settling.
3) The mixture was incubated at 80° C. for 20 minutes to inactivate the exonuclease.
4) Using magnetic separation, the beads were washed 5× with 200 µl of NX Buffer.
5) The beads were stored at 4° C. until use.

G. Single-stranding of Bead-bound Product with Sodium Hydroxide

It has been discovered that this step is important to allow efficient single-stranding of the bead-immobilized PCR products.
1) Remove all liquid from beads by magnetic separation
2) Add 50 µl 0.1M NaOH and mix with beads
3) Incubate 10 minutes at 25° C.
4) Wash once with 50 µl 0.1M NaOH
5) Wash twice with TE
6) Resuspend beads in 50 µl TE This protocol enables amplification of libraries that are several orders of magnitude more complex than libraries generated using bead-based methods known in the art.

Water-in-oil microemulsions may be prepared by dropwise addition of 200 µl of the aqueous phase to 400 µl of the oil phase in a 2-ml round-bottom cryogenic vial (no. 430661, Corning). The dropwise addition may be performed over 1 minute while the mixture is being stirred at 1,400 rpm with a magnetic microstir bar (no. 58948-353, VWR Scientific) on a VWR model 565 magnetic stirrer. After the addition of the aqueous phase, the mixture may be stirred for a total time of 30 minutes. Two emulsions can be made at once by placing two tubes in a rack placed at the center of the magnetic stirrer.

EXAMPLE II

Enrichment of Beads

The following protocol can be used to separate empty beads from clonal beads. The combined use of a low template concentration in the emulsion PCR reaction and the enrichment protocol resulted in a higher fraction of 'clonally amplified' beads than would otherwise be possible. The basis for enrichment was the use of a second set of large (3 micron diameter), non-magnetic beads (i.e., 'capture beads') that included a primer having a sequence identical to the 'reverse' PCR primer sequence (PR1-R). As sequence complementary to the reverse PCR primer will only be present on strands of DNA that are the product of the PCR reaction, amplified beads selectively hybridized to these large capture beads, whereas empty beads did not hybridize to capture beads efficiently. The 3 micron capture beads, hybridized to 1 micron amplified beads, were separated from the 1 micron empty beads on the basis of their differential density (e.g., by centrifuging beads through a density gradient solution).

Capture beads were prepared as follows: 50 µl of SPHERO™ polystyrene streptavidin-coated beads (non-paramagnetic, 3-micron diameter beads, Spherotech, Libertyville, Ill.) were pipetted into a 1.5 µl microcentrifuge tube, centrifuged at 13.2 krpm for 30 seconds to pellet, and resuspended in 50 µl of Bind & Wash buffer. The beads were centrifuged again, all liquid was drawn from the bead pellet, and the bead was resuspended in 49.5 µl of Bind & Wash buffer. 0.5 µl of 1 mM biotin-modified 'capture primer' PR1-R-BioXL: Biotin-5'-cgtaccccgcttggtctttctcccgtac-cccgcttggtctttctccCTGCCCCGGGTTCCTCATTCTCT (SEQ ID NO:4) was added. The beads were incubated for 20 minutes at room temperature with occasional mixing. The beads were centrifuged for 30 seconds to pellet, the liquid was removed, and 50 µl of Bind & Wash buffer was added. This wash step was repeated, and the beads were resuspended in 10 µl of Bind & Wash buffer. The capture beads were stored at 4° C. until use.

40 µl of 1-micron, processed beads in TE (mixture of amplified and unamplified beads generated in the above sections) was resuspended in 20 µl of Bind & Wash buffer. 10 µl of 3-micron capture beads was added to the 20 µl of 1-micron processed beads, and the beads were mixed by pipetting. Capture beads were hybridized to processed beads by incubating the mixture at 56° C. for 10 minutes. The mix was then carefully pipetted onto the top of 150 µl 60% glycerol (v/v) in a 1.5 µl microcentrifuge tube. The microcentrifuge tube was centrifuged for 1 minute at 13.2 krpm. Because of the differential density of the non-magnetic 3 micron beads and the magnetic 1 micron beads, the 3 micron beads remained in the supernatant (along with amplified 1 micron beads hybridized to them), while unhybridized, unamplified magnetic one micron beads formed a pellet at the bottom of the tube. The liquid was drawn out of the microcentrifuge (without disturbing pellet of beads at bottom of tube) and pipetted into a new microcentrifuge tube. The amplified beads, hybridized to the capture beads, were enriched in this supernatant.

Next, the enriched fraction of amplified one-micron beads was purified away from the capture beads. To the new tube containing the supernatant, 1 mL of water was added, mixed by pipetting, and centrifuged for 2 minutes at 13.2 krpm. All but 20 to 30 µl of liquid was drawn off, 50 µl of fresh water was added, mixed, and centrifuged again at 13.2 krpm for 2 minutes. All liquid was removed from the pellet of beads, and the beads were resuspended in 50 µl of 0.1M sodium hydroxide. The beads were incubated for 10 minutes with occasional mixing in order to dissociate the 1 micron beads from the 3 micron capture beads. A magnetic field was applied to the microcentrifuge tube to draw magnetic 1 micron beads to the side of the tube, and all supernatant was removed. The supernatant, which contained the 3 micron capture beads, was cloudy white. The 1 micron beads were washed once in 0.1 M NaOH and three times in 1× PCR buffer. The 1-micron beads were resuspended in 5 uL of TE and stored at 4° C.

Figure 2:
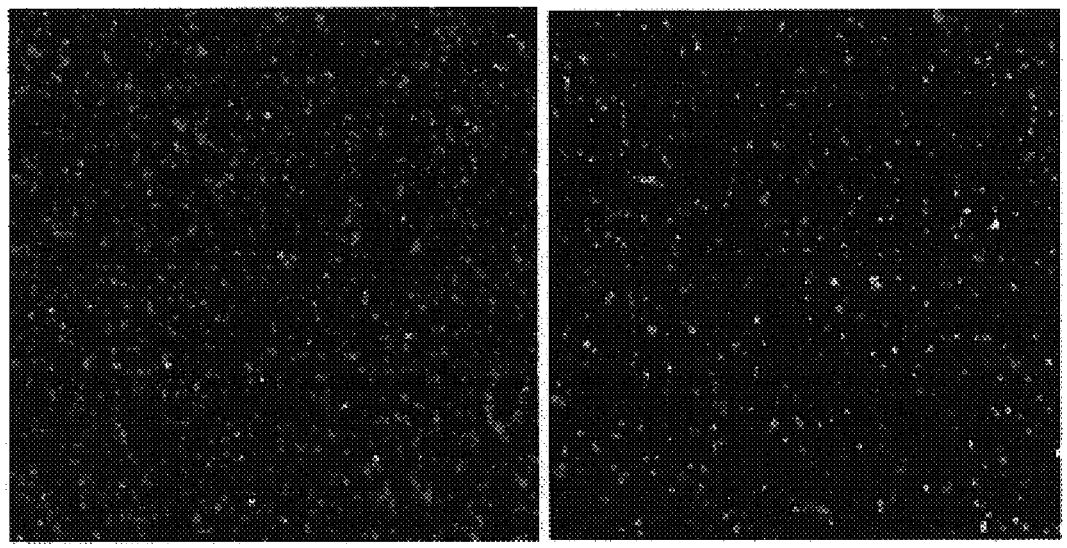
FIGS. 2A-2C depict beads that have undergone the enrichment protocol described herein. (A) depicts unenriched beads. Beads comprising amplified sequence ('amplified') are red and beads not having amplified sequence ('empty') are green. (B) depicts enriched amplified beads. (C) depicts beads from the pellet fraction showing a large percentage of empty beads.
Figure 2:
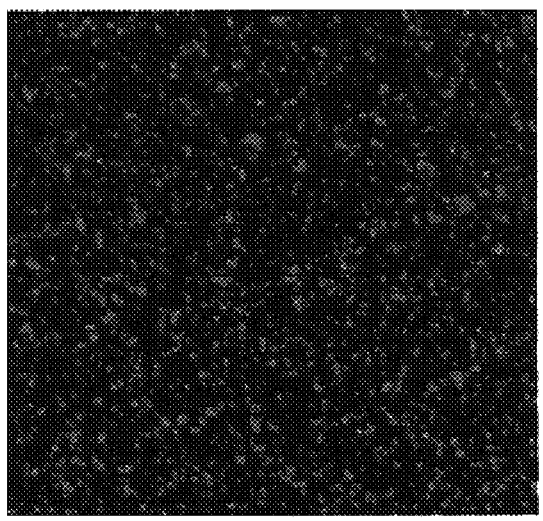

FIGS. 2A-2C depict a set of beads that went through the protocol as described above. The beads were taken from various steps to examine the fraction of beads that were amplified relative to those that were empty. In these pseudo-colored figures, green beads were empty and red beads were amplified. In the starting material of processed but unenriched one micron beads generated by emulsion PCR, approximately 8% of beads were amplified (FIG. 2A). In the set of beads that were eliminated by the above procedure, less than 1% were amplified (FIG. 2C). In the fraction of material enriched for amplified beads, the fraction of amplified beads had risen from 8% to 43% (FIG. 2B), a 5.5-fold enrichment.

EXAMPLE III

Monolayers of Disordered, Immobilized Beads

The critical nature of monolayering can be understood in the context of the depth of field of high resolution microscopes. For example, the depth of field with a 20× Plan Apo (NA=0.75) objective, one of the best commercially available objectives in terms of resolution is 1.9 microns. When clonal microspheres are only one micron in diameter, significant deviations from a monolayer would thus result in an inability to image arrayed beads while maintaining focus on all beads within a given field of view.

The following steps could take place before or after amplification (e.g., by a method for making populations of clonal microspheres), and optionally, after the bead enrichment protocol had been performed. Parallel sequencing or other forms of cyclic nucleic acid analysis would be carried out after the beads had been monolayered.

To form a monolayers of beads, the following protocol was used. The following reagents were mixed: 3.00 µl of beads (at desired density); 5.10 µl of dH$_2$O; 1.50 µl of acrylamide:bis (38% acrylamide, 2% bis-acrylamide; Roche); 0.60 µl of RHINOHIDE™ (polyacrylamide gel strengthener) (Molecular Probes, Eugene, Oreg.); 1.20 µl of 5% N,N,N',N'-tetramethylethylenediamine (TEMED); and 1.80 µl of ammonium persulfate solution (APS) (0.5%).

The mixed reagents were poured between a teflon-coated microscope slide and a coverslip, and allowed by polymerize, resulting in a 30 micron thick gel. Either the coverslip or the microscope slide was coated with Bind Silane (3-Methacryloxypropyltrimethoxysilane), such that the gel will stick to either the microscope slide or to the coverslip after polymerizing. The protocol for coating a glass surface in Bind Silane is described in Mitra et al. (Id.), for example. In brief, 220 µl of acetic acid and 4 mL of Bind Silane reagent were mixed into 1 liter of dH$_2$O. The glass surface was exposed to this solution via immersion for 1 hour with gentle shaking. Glass surfaces were washed by immersion three times in dH$_2$O and once in 100% ethanol. Slides were allowed to air-dry and were stored dessicated.

Figure 3:
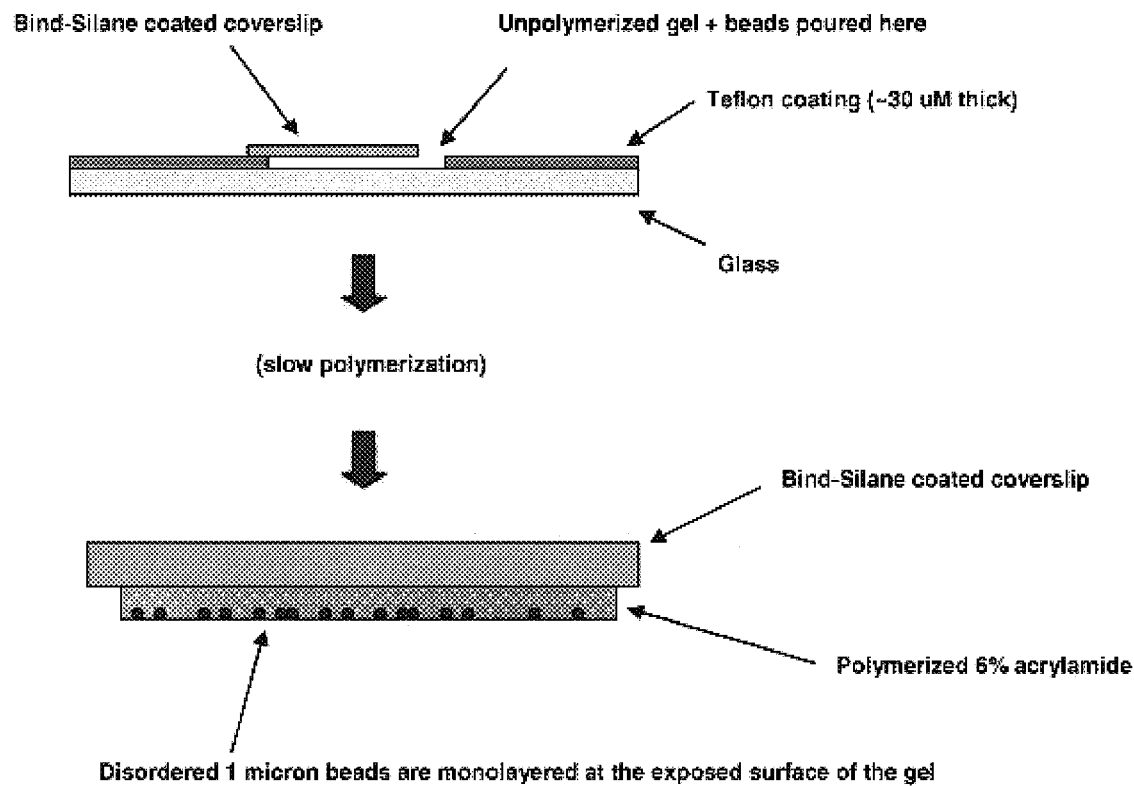
FIG. 3 depicts a schematic of the monolayering protocol described herein.

During polymerization, the microscope slide and polymerizing gel were placed in an orientation such that the beads would settle towards the desired side of the gel. Thus, the beads would form either a 'top layer' or a 'bottom layer' with respect to the exposed surface of the gel (FIG. 3). For performing hybridization and enzymatic reactions on DNA immobilized to the beads, it has been discovered that the beads in a 'top layered' gel are much more accessible to enzymes and oligonucleotides applied to them, permitting much more efficient reaction kinetics. This is not surprising, as many of the enzymatic reactions used to query the gel are performed by enzymes that would have difficulty accessing the beads if they were actually deep within the gel. The gel was 30 microns thick while the beads were only one micron thick. Although the gel pores were large, diffusion of enzymes and or oligonucleotides through them would be slow if the beads sat at the bottom of the gel, for example.

The final product consisted of a glass surface to which the acrylamide gel was attached via the Bind Silane reagent (FIG. 3). The gel was approximately 30 microns thick. The beads were present in a monolayer at the top of the gel (i.e. most distal from the glass coverslip to which the gel is attached via the Bind-Silane).

This example provides that the concentrations of the catalyzing agents (APS and TEMED) are much lower than what is typically used in the art to polymerize gels, such that after the gel is poured, it will polymerize at a slow rate (about one hour) allowing the beads to settle via gravity into a monolayer at one surface of the gel. It has been determined that if the polymerization process is too rapid, the beads do not have time to settle into a monolayer, and the result is a layer of beads that cannot be visualized in a single focal plane. The act of inverting the polymerizing gel such that the beads settle in a monolayer at the exposed surface of the gel is advantageous for enabling enzymatic reactions that are subsequently used to manipulate the DNA on the beads.

A motivation for using 'ordered' arrays of beads or other substrates (i.e., the bead-based arrays of the art) has been the desire to make repeated independent observations of the same feature, or desire for 'addressability', typically taking the form of an ordered array with Cartesian coordinates. The arrays described in this example are ordered with respect to the Z-axis, in that they are monolayered, but disordered with respect to the X and Y axes. Individual beads have been visualized and distinguished at high densities and repeated, independent observations have been made of a given subsection of the gel, which have been aligned to previous observations of the same subsection of the gel, thus allowing multiple independent observations of individual beads within each subsection. Bead positions remained invariant even with numerous enzymatic manipulations, exposure to 95° C. heat, and the like. The use of disordered monolayers thus avoids many of the difficulties associated with generating ordered arrays while accomplishing the same goal.

EXAMPLE IV

Primer Hybridization and Sequencing by Single Base Extension

At this step in the protocol, the beads reside in a monolayer at the exposed surface of an acrylamide polymer gel that is itself attached to a glass coverslip. The DNA on the surface of the beads can thus be easily exposed to a variety of reagents and conditions without disturbing their absolute positions in the gel. It has been discovered that a variety of enzymatic and chemical reactions can be performed on DNA immobilized in this format including, but not limited to, sequence-specific oligonucleotide hybridization, polymerase-driven primer-extension, restriction endonuclease-driven sequence-specific cleavage, ligase-driven oligonucleotide ligation, exonuclease-driven DNA degradation and the like.

As an example of these enzymatic reactions, the protocol for hybridizing a oligonucleotide primer and then performing a polymerase-driven single-base-extension with a fluorescent nucleotide is described.

As the PCR products on the bead have been single-stranded, they now consist, from 5' to 3', of the double-biotin moiety immobilizing the strand to the beads, the PR1-F forward primer sequence, unknown sequence (dependent on material from which library was constructed, and variable from bead to bead), and sequence complementary to the PR1-R primer. To hybridize the PR1-R primer to the bead-immobilized DNA, 100 µl of 1 µM PR1-R in Hybridization Buffer (6×SSPE with 0.01% TRITON® X-100) was applied to the gel, and the liquid was sealed into contact with the gel using a 125 µl FrameSeal chamber. The slide was heated at 56° C. for 10 minutes, the FrameSeal chamber was removed, and the slide was immersed in 1× Wash Buffer (10 mM Tris, pH 7.5; 50 mM KCl; 2 mM EDTA; 0.01% TRITON® X-100). The slide was incubated with shaking for 2 minutes in wash, and washed twice more in 1× Wash Buffer. The PR1-R primer was thus hybridized to DNA. The 3' end of the PR1-R primer was positioned immediately adjacent to the unknown sequence of the bead-immobilized molecules.

To query the identity of the first unknown base by polymerase-driven single-base-extension, the following mix was prepared, containing both polymerase and fluorophore-labeled ddNTPs: 122 µl of 1× ThermoSequenase™ Buffer (Amersham Biosciences, Piscataway, N.J.); 1 µl of ThermoSequenase™ (4 u/uL, Amersham Biosciences); 0.5 µl of R110-ddGTP (100 µM, PerkinElmer, Wellesley, Mass.); 0.5 µl of Cy5-ddCTP (100 µM, PerkinElmer); 0.5 uL of Cy3-ddUTP (100 µM, PerkinElmer); and 0.5 µl of Texas-Red ddATP (100 µM, PerkinElmer).

The mixture was applied to the slide as above using a 125 µl FrameSeal chamber, and incubated at 42° C. for 5 minutes to extend. The immersion was washed in 1× Wash Buffer for 2 minutes with slow shaking at room temperature, and the wash was repeated 1 to 2 times before imaging. Imaging was performed on an epifluorescence microscope equipped with the a xenon lamp light-source and the appropriate set of filters for the fluorophores used herein. Each bead emitted fluorescence with filters corresponding to only one of the four fluorophores, revealing the identity of the incorporated base and thus of that unknown position in the DNA sequence.

EXAMPLE V

Imaging on Epifluorescence Microscope

The beads were immobilized on a gel which was immobilized to a glass coverslip. The gel and the glass could both be imaged through. It has been determined that the acrylamide gel, at the % that was used did not cause significant autofluorescence or interference with light transmission.

To image fluorescent moieties incorporated into or on molecules associated with DNA immobilized to the beads, an epifluorescence microscope (Nikon TE2000) with an automated X-Y stage (Prior) and focus control was used. Epifluorescent illumination was by either a mercury arc lamp, a xenon arc lamp, or a mercury halide arc lamp. Images were acquired by a CCD-based detector mounted on the microscope. Either long working distance objectives or high-numerical aperture objectives were used, with typical magnifications from 10× to 40×. Typically, the beads were immobilized in a gel which was attached to a microscope slide. Alternatively, the immobilized bead-gel was occasionally attached to a glass coverslip which mounted in a flowcell or a microscope slide which mounts in a flowcell. Either the flowcell or microscope slide fit into a detail in the stage. In the case of the microscope slide, the slide could be removed from the microscope between cycles of image acquisition to perform experimental protocol (e.g., sequencing). One problem associated with removing the slide from the stage between image acquisition cycles is the inability to accurately reposition the slide on the microscope stage with micron accuracy. Typically, one could expect a repositioning error of 100 microns or more. This error, at 40× magnification with 7 micron CCD pixel size, would result in a data loss of 75% or more due to image misalignment from one cycle to the next. It should be noted that this problem can also occur to a lesser extent if the slide or flowcell is not removed from the microscope, but an experimental protocol is performed which involves fluctuations in temperature of the slide or flowcell. Such temperature changes will induce mechanical changes in the geometry of the slide or flowcell and can result in image misalignment. To allow accurate re-positioning of the microscope stage in the X, Y, and Z axes after successive cycles of imaging and slide removal to within several microns in X and Y, and less than a micron in Z the following steps may be used:

Step 1

At the start of the experiment, a 'focal map' of the surface to be imaged was generated. This focal map is a list of x, y, z coordinates on the bead array for the microscope to visit during each acquisition cycle. This focal map is normally generated by executing an 'auto focus' routine at each x, y position in the list to generate the corresponding z position. The auto focus algorithm used is implemented by the META-MORPH® acquisition software (Universal Imaging Corporation, Downingtown, Pa.) and uses either transmitted brightfield images, reflected brightfield images, or epifluorescence images where beads of interest have been labeled with a fluorescent molecule or molecules.

Step 2

At the start of each imaging cycle, the software returned to the first x, y, z hardware position in the focal map. The auto focus routine was executed for that particular field of view to compensate for positioning error in the z axis. An image was then acquired and passed to an image registration software program which found the appropriate offsets in the x and y axes to translate the new image in order to bring it into registration with the original image of that frame (to within a pixel; distance in microns is given by the pixel size, normally approximately 7 μm). Since the beads were immobilized, they could serve as fiducial markers, obviating the need for introduction of additional features in the array. Thus, having disordered beads was a strong advantage when one is performing precise image alignment. The microscope stage was then moved in x and y by these offsets. The bead array was then at an x, y, z position close to the original position from Step 1. It has been discovered that images can be brought into alignment with sub-micron resolution using this method. A second auto focus was performed to ensure that the new x, y position was in focus. The origin was reset at this new position.

Step 3

Figure 4:
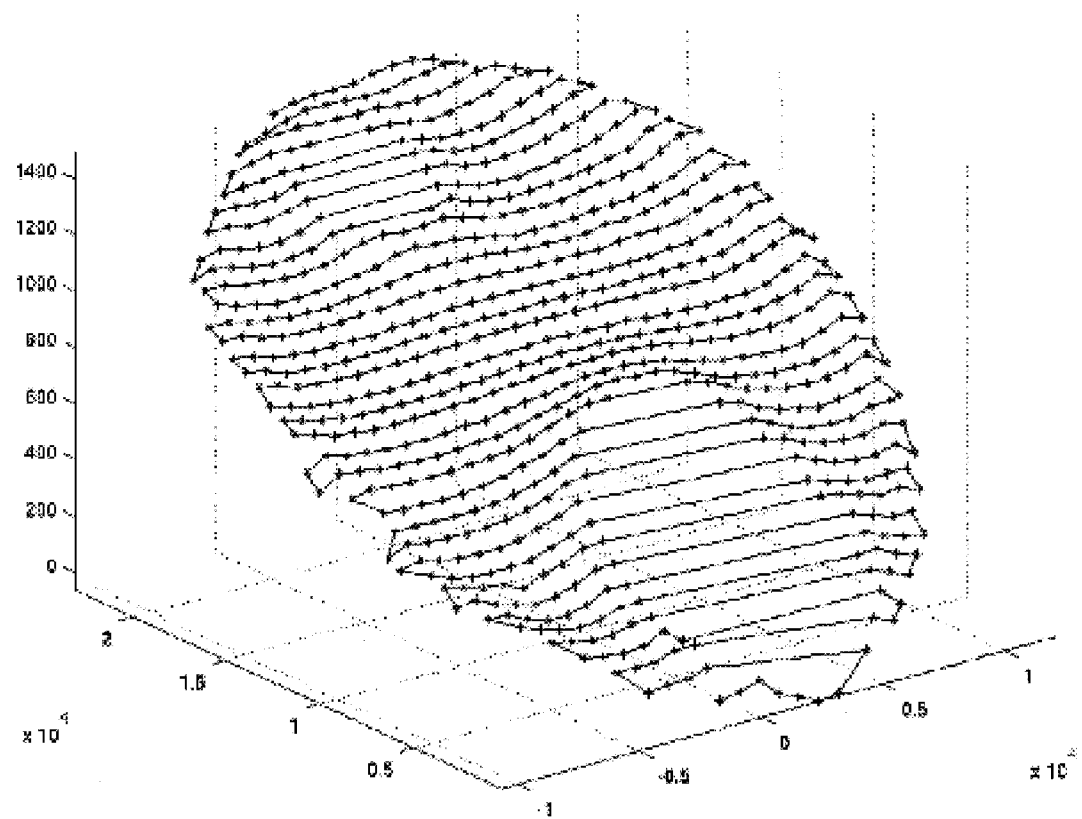
FIG. 4 depicts a focal map.
Figure 5:
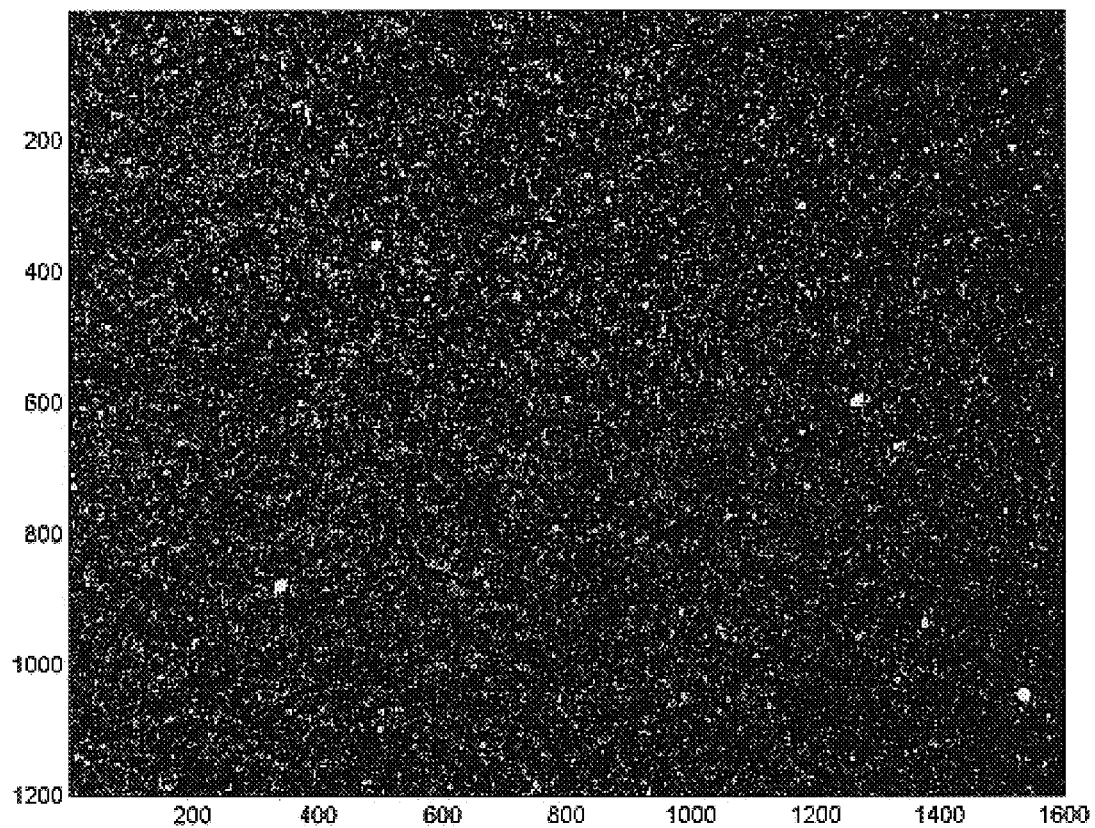
FIG. 5 depicts an image of monolayered beads with transmitted bright-field at high density.

Images were acquired by visiting each position in the original focal map. These images were be in register with all previous cycles, allowing extraction of data for most or all beads in every frame. An example of plotted coordinates of a typical 'focal map' is set forth in FIG. 4, which shows a circular gel (approximately 1 cm in diameter) with two large holes. Red points indicate the relative XYZ coordinates of individual frames. FIG. 5 depicts a sample image of monolayered beads at imaged with transmitted bright-field at high density.

EXAMPLE VI

Paired-Tag In Vitro Library Construction

Figure 11:
FIG. 11 depicts a schematic of end-products of library construction.

An in vitro library construction protocol has been developed that results in a pool of linear dsDNA molecules, where each molecule is approximately 134-136 bp in length, and includes a unique pair of 17-18 bp tags derived from the genome-of-interest. These unique tags are flanked by a set of sequences complementary to universal primers (PR1-R and PR1-F) and separated by an additional universal spacer sequence ("T30") (FIG. 11). The unique tags are "paired" in that they are identically oriented on the genome-of-interest and their separation on the genome-of-interest falls within a constrained range (e.g. 1000+/−100 bases). The protocol is unique in that it is entirely in vitro; no transformation into *E. coli* is required.

A library in this format constructed by in vitro methods, provides the following benefits over conventional genomic shotgun sequencing: (a) the emulsion PCR protocol is considerably more efficient for amplifying short sequences; thus there is a motivation to minimize the total length of each amplifiable molecule in the library; (b) the experience of Sanger-based genome projects indicate that paired reads are immensely useful for genomic re-sequencing, especially when a genome contains repetitive elements; (c) the methods described herein rely on the positioning via an universal 'anchor' sequence. In this library format there are both proximal and distal anchors for two tags, effectively enabling one to double read-lengths by applying the sequencing methods independently for each tag.

The library construction protocol had the following steps:
1. purification of genomic DNA
2. shearing of genomic DNA to generate fragments
3. end-repair and A-tailing of DNA fragments
4. PAGE size-selection of sheared fragments
5. circularization with T-tailed spacer oligonucleotide ("T30")
6. rolling circle amplification (RCA) with random hexamers
7. digestion with MmeI (type IIs) to release paired tags
8. PAGE purification of tag-T30-tag library
9. end-repair of tag-T30-tag library
10. ligation of FDV2 (PR1-F) and RDV2 (PR1-R) primer oligonucleotides
11. PAGE size-selection of paired-tag library
12. nick translation to eliminate nicks in dsDNA library
13. PCR amplification of paired-tag library
14. PAGE size-selection of paired-tag library
15. Library validation via cloning and Sanger sequencing Detailed protocols for each of the above steps are given below, as they were performed for constructing paired-tag libraries for the "M" and "R" *E. coli* strains.

Purification of Genomic DNA

For each of *E. Coli* strains "M" and "R", cultures were grown overnight in 3 mL of LB and isolated with the Qiagen DNEASY® Tissue kit as per the manufacturer's protocol. Yield for each genomic DNA purification was approximately 30 μg (Qiagen Inc., Valencia, Calif.).

Shearing of Genomic DNA to Generate Fragments with a Broad Size Distribution

Figure 12:
FIG. 12 depicts a polyacrylamide gel electrophoresis (PAGE) gel for size selection of sheared fragments, post-cutting.

Shearing of genomic DNA from both strains was performed by Agencourt Bioscience Corporation (Beverly, Mass.). The size-distribution of the resultant DNA fragments was quite broad, as can be seen on the gel below (FIG. 12).

End-Repair and A-Tailing of DNA Fragments

Unless stated otherwise, all DNA quantitation was performed on a Nanodrop ND-1000 Spectrophotometer.

Sheared genomic "M" DNA was quantitated at 57 ng/μl, and sheared genomic "R" DNA was quantitated at 55 ng/μl. Sheared DNA fragments were end-repaired with the EpiCentre END-IT™ DNA End Repair Kit (Madison, Wis.). For each library, the following mix was prepared: 170 μl of sheared *E. coli* DNA (~9-10 μg); 25 μl of 10× END-IT™ Buffer; 25 μl of 10× END-IT™ ATP; 25 μl of 10× END-IT™ dNTPs; and 5 μl of END-IT™ Enzyme for a total volume of 250 μl.

Reactions were incubated at room temperature for 1 hour. DNA was purified on a Qiagen QIAQUICK® column as per manufacturer's recommendations for PCR product purification. Approximately 90 μl of Buffer EB (10 mM Tris.cl, pH 8.5) was used for elution. "M" DNA was quantitated at 96.5 ng/μl, and "R" DNA was quantitated at 75.1 ng/μl. Each volume was split to 4 tubes of approximately 22 μl. To eliminate residual enzyme activity, tubes were heated to 70° C. for 15 minutes. An A-tailing master-mix was prepared as follows: 100 μl of 10× PCR buffer (no $MgCl_2$) (Invitrogen, Carlsbad, Calif.); 60 μl of 50 mM $MgCl_2$ (Invitrogen) (final concentration of 3 mM); 5 μl of 100 mM dATP (Invitrogen) (final concentration of 0.5 mM); 5 μl of Taq (5 U/uL) (New England Biolabs, Beverly, Mass.); and 610 μl of $dH_2O$.

After heat-inactivation, 78 μl of the master-mix was added to each tube containing 22 μl of sheared, end-repaired DNA fragments. Tubes were incubated at 70° C. for 30 minutes in a thermal cycling machine. The cycling program ended by cooling the tubes to 4° C. The tubes were and then transferred from the thermal cycler directly to ice.

DNA was purified by phenol-chloroform extraction and ethanol precipitation (P:C:P) as follows:
1. Added an equal volume of phenol: chloroform: isoamyl alcohol (25:24:1)
2. Added 0.1 volume of 3M NaOAc (pH 5.2)
3. Added 1.0 μl of glycogen (20 μg/μl)
4. Added 2.5 volumes of cold 100% ethanol (from bottle stored at −20° C.)
5. Mixed by inverting
6. Put tube at −70° C. for ~30-60 minutes 7. Spun at maximum speed on microcentrifuge in 4° C. room for 10 minutes
8. Removed supernatant
9. Added 1 ml of 80% ethanol
10. Spun at maximum speed on microcentrifuge at room temperature for 5 minutes
11. Removed supernatant
12. Placed tube on Speed-Vac for ~5 minutes
13. Resuspended pellet in 40 µl Buffer EB or TE PAGE Size-Selection of Sheared Fragments Half of the material from each library was loaded in a pre-cast 6% TBE-PAGE gel (Invitrogen, Carlsbad, Calif.). 20 µl of DNA was mixed with 5 uL of 5× High-Density Sample Buffer (Novex, San Diego, Calif.). The same loading buffer was used for all subsequent PAGE gels in this protocol. 12.5 µl of the sample/loading buffer mixture was loaded per lane (two lanes per library). The gel was run on standard apparatus and a region corresponding to approximately 1000 base pair fragments was cut out with minimal exposure to UV. Gel fragments were diced with razor and each library's fragments transferred to 600 µl of PAGE elution buffer (10 mM Tris-HCl (pH 7.5), 50 mM NaCl, 1 mM EDTA (pH 8.0)). Tubes were incubated at 37° C. overnight.

The following day, th e elutions were spun for one minute at maximum speed in a microcentrifuge and the supernatants were transferred to new tubes. To improve recovery, washed gel fragments with an additional 200 uL of PAGE buffer. DNA was purified using the P:C:P protocol, and each pellet was resuspended in 22 µl of Buffer EB.

The A-tailing step was repeated to minimize the impact of potential partial degradation of the A-tails that may have occurred during the gel purification. Both end-repair and A-tailing may be performed after the PAGE-based size-selection, rather than before. An A-tailing master-mix was prepared as follows: 25.00 µl of 10× PCR buffer (no $MgCl_2$); 15.00 µl of 50 mM $MgCl_2$ (final concentration of 3 mM); 1.25 µl of 100 mM dATP (final concentration of 0.5 mM); 1.25 µl of Taq (5 U/µl); and 152.50 µl of $dH_2O$.

78 µl of the A-tailing master-mix was added to each tube containing DNA resuspended in 22 µl for total volume of 100 µl. For each library, this was split into two thermal-cycler compatible tubes of 50 µl each. Tubes were incubated at 70° C. for 30 minutes in a thermal cycling machine. The cycling program ended by cooling the tubes to 4° C. The tubes were then transferred from the thermal cycler directly to ice. DNA was purified by P:C:P protocol. Each library was resuspended in 10 µl of Buffer EB and put on ice.

Figure 13:
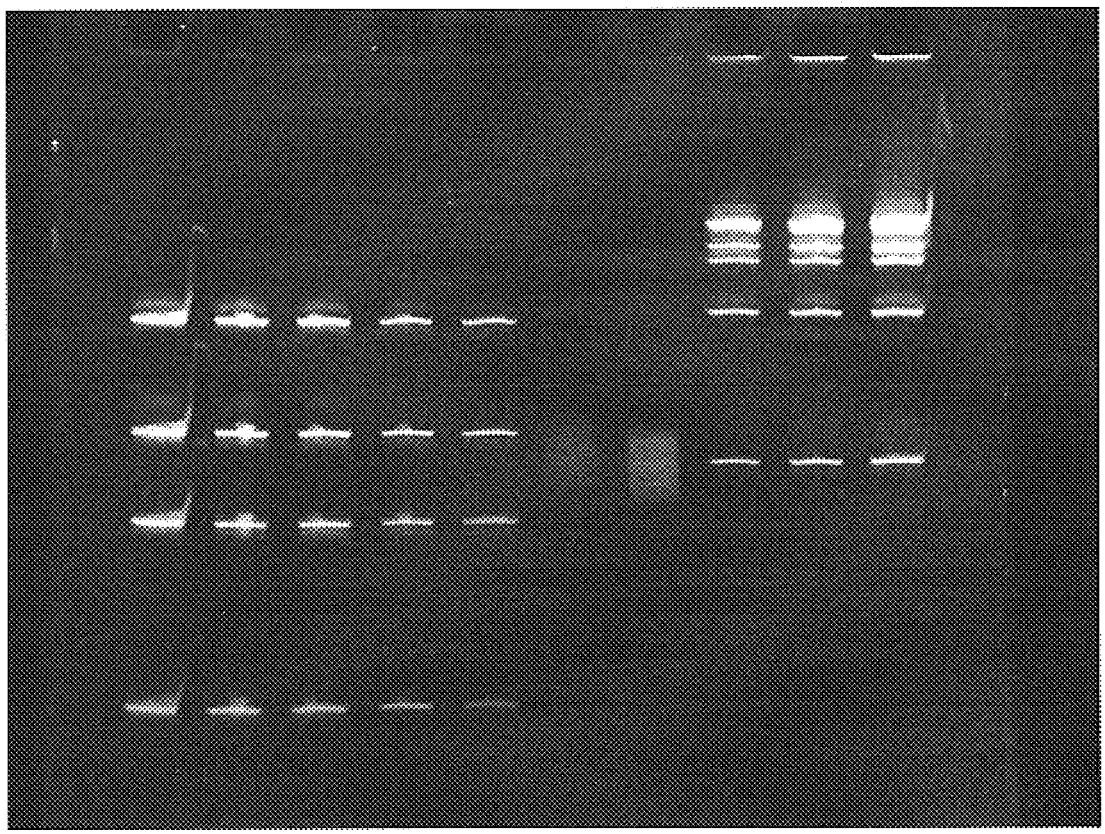
FIG. 13 depicts a PAGE gel for quantitating size-selected fragments.

To quantitate recovery and estimate the size-range of recovered fragments, a pre-cast 6% TBE PAGE gel (Invitrogen) was run using 20% of the purified material (FIG. 13). Gel-based quantitation of "M"=43 ng (in 2 µl, or 20% of the total); range=approximately 850-1150, mean=approximately 1000. Gel-based quantitation of "R"=18 ng (in 2 µl, or 20% of the total); range=approximately 900-1250; mean=approximately 1075. In the remaining approximately 8 µl volume retained for each library, there was approximately 171 ng of "M" fragments and approximately 73 ng of "R" fragments.

Circularization with T-Tailed Spacer Oligonucleotide ("T30")

Next, the A-tailed library fragments were circularized using the T-tailed spacer oligonucleotide "T30". The T30 segment was prepared by annealing two 32-bp oligonucleotides to generate a 30 bp dsDNA fragment with single base "T" overhangs:

(SEQ ID NO: 5)
5' GTCGGAGGCCAAGGCGGCCGTACGTCCAACT 3'

(SEQ ID NO: 6)
3' TCAGCCTCCGGTTCCGCCGGCATGCAGGTTG 5'

The T30 segment is flanked by outward-facing MmeI sites.

Annealing of the oligos was performed by mixing to a final concentration of 50 µM for each oligo, heating to 95° C. for 10 minutes in a thermal cycler, shutting the thermal cycler off and allowing the mixture to cool slowly back to room temperature over the course of an hour.

Ligation of the T30 fragment with the A-tailed library fragments was performed using a QUICK LIGATION™ kit (New England Biolabs, Beverly, Mass.). Reactions were prepared as follows. "M" library circularization reaction (total volume of 80 µl): 8.0 µl of A-tailed fragments from "R" tube (~171 ng at 1000 bp=0.2599 pmol); 27.2 µl of $dH_2O$; 0.8 µl of T30 (1 µM starting concentration (0.8 pmol, 3-fold molar excess)); 40.0 µl of 2× QUICK LIGATION™ Buffer; and 4.0 µl of QUICK™ T4 DNA ligase. "R"library circularization reaction (total volume of 30 µl): 8.0 µl of A-tailed fragments from "R" tube (~73 ng at 1075 bp=0.1032 pmol); 5.2 µl of $dH_2O$; 0.3 µl of T30 (1 µM starting concentration (0.3 pmol, 3-fold molar excess)); 15.0 µl of 2× QUICK LIGATION™ Buffer; 1.5 µl of QUICK™ T4 DNA ligase. Each reaction was mixed well before and after adding enzyme to each tube. The reactions were incubated for 10 minutes at room temperature, then moved to ice.

The ligase was heat-inactivated on a thermal cycler at 65° C. for 10 minutes. To destroy all non-circularized material, an exonuclease mix was added. The exonuclease mix is prepared as follows: 4.0 µl of Exonuclease I (20 U/µl) (New England Biolabs, Beverly, Mass.); 0.4 µl of Exonuclease III (100 U/µl) (New England Biolabs, Beverly, Mass.); and 35.6 µl of TE. 10 µl of exonuclease mix was added to the 80 µl "M" reaction, and 3.75 µl of exonuclease mix was added to the 30 µl "R" reaction. The tubes were incubated for 45 minutes on a thermal cycler at 37° C., followed by 80° C. for 20 minutes to heat-inactivate the exonucleases. This material was used directly in the RCA reaction of the next step without any purification.

Rolling Circle Amplification (RCA) with Random Hexamers

Hyperbranched RCA was performed to amplify the amount of library material using the REPLIPHI™ phi29 kit (EpiCentre, Madison, Wis.). A master-mix was prepared as follows: 32.0 µl of dNTP mix (25 µM each); 80.0 µlof 10× REPLIPHI™ phi29 reaction buffer; 40.0 µl of random DNA hexamers (1 mM, synthesized as 5'-NNNN*N*N-3', where "*" indicates phosphorothioate linkage); 552.0 µl of $dH_2O$; and 16.0 µl of 5× SybrGreen. The master-mix was split into two tubes of 270 µl, to which either 30 µl of "M" or "R" material was mixed for a total volume of 300 µl. Each tube was then split into 6 tubes of 50 µl. To denature circularized template, the tubes were heated to 95° C. for 5 minutes, followed by rapid cooling to 4° C. 2.5 µl of phi29 enzyme was added to each tube on ice for total volume of 52.5 µl per tube. The tubes were mixed well and kept on ice. The tubes were incubated overnight at 30° C. in the thermal cycler.

The RCA reactions were run on a real-time PCR machine, and amplification was observed via the SybrGreen dye present in the reaction. The dsDNA content had risen and leveled off by the 2-hour time-point, indicating that running the reaction overnight may not be necessary.

DNA was purified with a MICROCON-30® column (Millipore, Billerica, Mass.), washing with a total of 1 mL of TE.

The pellet was substantial. Several washings of the MICRO-CON-30® membrane were used to maximize recovery. A combination of heating at 50° C. and adding additional resuspension buffer (Buffer EB) was used to resuspend the DNA. Approximately 750 uL of each library was recovered.

Samples were quantitated on a NANODROPO® instrument (NanoDrop Technologies, Wilmington, Del.): "M"=230 ng/uL and "R"=204 ng/uL. The RCA reaction thus resulted in ~150 µg of each library.

Digestion with MmeI (type IIs) to Release Paired Tags

Approximately 40 µg of each library was digested with MmeI. As the MmeI site cuts at a distance from its recognition site in the T30 segment, and there are outward-facing MmeI sites at either end of the T30 segment, this digestion was expected to release the T30 segment flanked by ~18 bp tags with 2 bp overhangs (~70 bp in length). Because genomic fragments were circularized with T30 prior to MmeI digestion, these tags were expected to be paired with respect to the positions of their origin.

Reactions were prepared as follows. MmeI, S-adenosyl-methionine (SAM), and NEBuffer 4 (10×) were obtained from New England Biolabs (Beverly, Mass.). 32 mM SAM was diluted 1:20 (−>1.6 mM) in 1× NEBuffer 4.

TABLE 1

|  | Reaction "M" | Reaction "R" |
|---|---|---|
| DNA | 173.9 | 196.0 |
| dH$_2$O | 664.5 | 642.4 |
| NEBuffer 4 (10x) | 100.0 | 100.0 |
| 1.6 mM SAM | 1.6 | 1.6 |
| MmeI (2 U/µl) | 60.0 | 60.0 |
| total volume (µl) | 1000.0 | 1000.0 |

Figure 14:
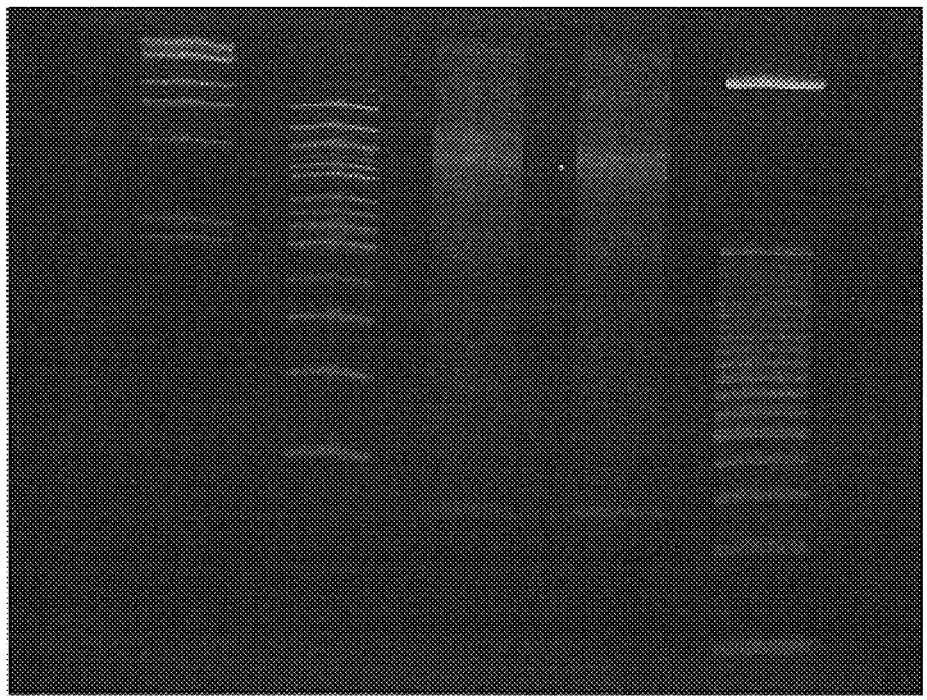
FIG. 14 depicts a diagnostic 6% PAGE gel of MmeI digested rolling circle amplification (RCA) material.

Reactions were prepared on ice, and reagents were well-mixed prior to adding enzyme. Each reaction was split to 8 tubes of 125 µl, and incubated on a thermal-cycler for 30 minutes at 37° C. P:C:P purification as described in above, except using only 2 volumes of ethanol instead of 2.5 volumes, without heat-inactivating first. Digested fragments for each library were resuspended in 80 µl of TE. A band at approximately 70 bp was observed in the "M" and "R" lanes, as expected (FIG. 14).

PAGE Purification of Tag-T30-Tag Library

Figure 15:
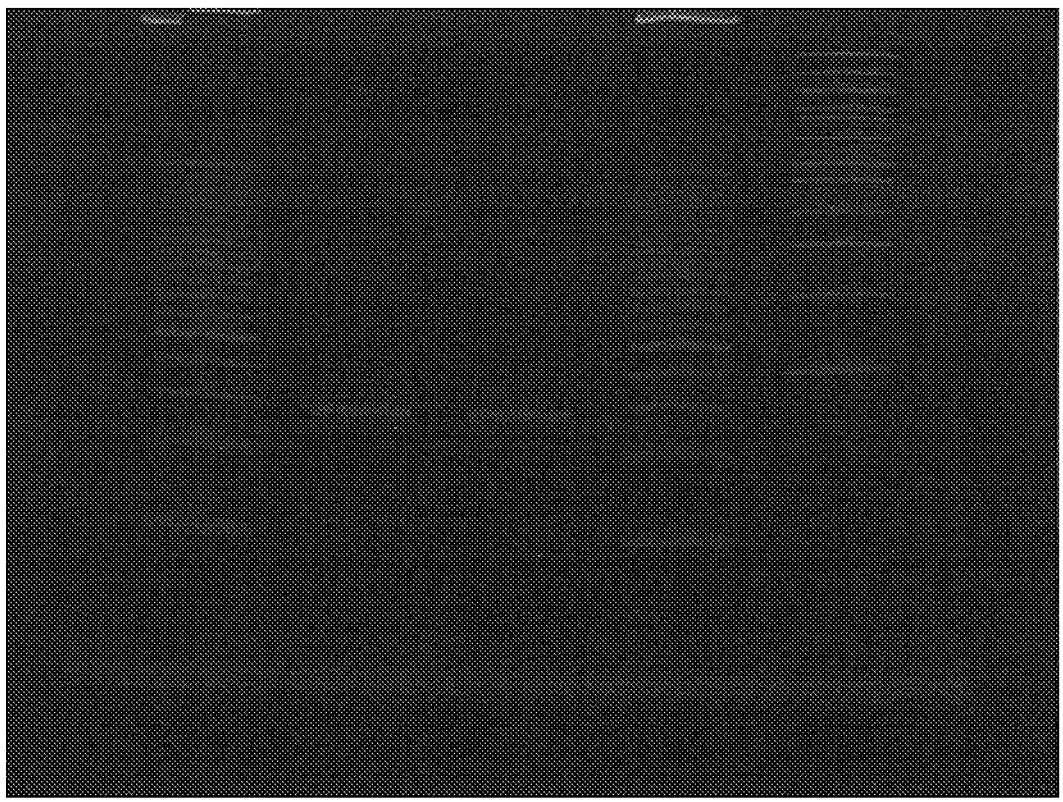
FIG. 15 depicts a diagnostic 6% PAGE gel of a gel purified, primerless library.

The full amount of each library was run on a 10-lane pre-cast 6% PAGE gel as above, using 4 lanes per library (20 µl of library and 5 µl of 5× dye). A sharp band at approximately 70 base pairs was cut. Fragments from all lanes of each library type were combined, and the gel-extraction was carried out as described above, except elution was for approximately 3 hours. After P:C:P recovery, the DNA for each library was resuspended in approximately 20 µl of TE. A diagnostic gel was run to quantitate the recovered material (FIG. 15). Both the "M" and "R" libraries were estimated at approximately 12.5 ng/µl, and 18 µl of each remained at this point.

End-Repair of Tag-T30-Tag Library

The tag-T30-tag molecules contained 2 bp 3'-overhangs, consequent to MmeI digestion. The ends were repaired using EpiCentre END-IT™ DNA End Repair Kit as described above (Madison, Wis.). Reactions were prepared as follows: 8.50 µl of "M" or "R"fragments (12.5 ng/µl: approximately 100 ng); 1.25 µl of 10× END-IT™ Buffer; 1.25 µl of 10× END-IT™ ATP; 1.25 µl of 10× END-IT™ dNTPs; and 0.25 µl of END-IT™ Enzyme for a total volume of 12.5 µl.

Reactions were incubated at room-temperature for 45 minutes, then moved directly to 4° C. Volumes were increased to 50 µl by adding 40 µl of TE, and the reactions were P:C:P extracted as described above. The precipitation step was allowed to go overnight at −70° C. Recovered DNA was resuspended in 8 µl of TE.

Ligation of FDV2 (PR1-F) and RDV2 (PR1-R) Primer Oligonucleotides

The primer-adaptors (dsDNA, FDV2 and RDV2) were prepared by annealing fully complementary oligonucleotides (100 µM, HPLC-purified) by mixing 1:1 (final concentration of 50 µM), heating to 95° C. for 10 minutes, and allowing the reaction to cool slowly over the course of an hour.

In "annealed" format, FDV2 and RDV2 were as follows:

FDV2:

(SEQ ID NO: 7)
5'-AACCACTACGCCTCCGCTTTCCTCTCTATGGGCAGTCGGTGAT (SEQ ID NO: 8)
3'-TTGGTGATGCGGAGGCGAAAGGAGAGATACCCGTCAGCCACTA

RDV2:

(SEQ ID NO: 9)
5'-AACTGCCCCGGGTTCCTCATTCTCT (SEQ ID NO: 10)
3'-TTGACGGGGCCCAAGGAGTAAGAGA

The FDV2 and RDV2 molecules were unphosphorylated, and therefore were not expected to be able to self-self ligate nor to ligate to one another. The end-repaired ligated molecules were phosphorylated, and therefore, an excess of FDV2 and RDV2 was used to minimize concatamerization events for library molecules. Ligations of primer-adaptors to the library molecules were blunt-blunt and therefore conducted in the presence of polyethylene glycol (PEG) to improve ligation efficiency. Each reaction was set up as follows: 12.3 µl of dH$_2$O; 8.0 µl of purified, blunted library fragments ("M" or "R"; approximately 100 ng, i.e., approximately 2 pmol); 1.0 µl of RDV2 (50 µM, 50 pmol); 1.0 µl of FDV2 (50 µM, 50 pmol); 2.5 µl of 10× T4 Ligase Buffer (New England Biolabs, Beverly, Mass.); 21.2 µl of 40% PEG (40% polyethylene glycol 8000); and 2.0 µl of T4 Ligase (2000 U/µL) (New England Biolabs). Reactions were prepared at room-temperature by mixing all reagents except the PEG and ligase. The PEG was then added and mixed in, and the ligase was added and mixed in. Reactions were incubated at 16° C. overnight. To purify, reaction volumes were increased to 100 µl with TE and P:C:P purified. Pellets were resuspended in 10 µl of Buffer EB.

PAGE Size-Selection of Paired-Tag Library

Entire reactions were run on a 10 well 6% PAGE gel along with the appropriate ladders. The gel was run far enough such that unligated RDV2 and FDV2 (present in great molar excess relative to the library) were expected to have run off the gel. A triplet of bands of the appropriate size was observed as expected (resulting from RDV2/library fragment/RDV2 ligation, RDV2/library fragment/FDV2 ligation, or FDV2/library-fragmentlFDV2 ligation). The regions containing the full triplets were cut and gel-purified as described above, except elution was for three hours, and ethanol precipitation was overnight at −70° C. Samples were each resuspended in 20 µl of Buffer EB.

Nick Translation to Eliminate Nicks in dsDNA Library

As only the library molecules were 5'-phosphorylated in the ligation, the ligation products were expected to contain nicks that must be repaired. Moving forward with half of the remaining material, nick translation was performed as follows: 10.0 µl of library (assuming 100% recovery, this should be 50 ng of tag-T30-tag molecules plus the mass of ligated primer-adaptors); 0.5 µl of dNTP mix (25 mM, so final concentration of 500 µM for each nucleotide); 2.5 µl of 10× NEBuffer-2 (New England Biolabs); 1.0 µl of E. coli DNA polymerase I (10 U/µl) (New England Biolabs); and 11.0 µl of dH$_2$O. Reactions were prepared and mixed on ice, and then incubated at 16° C. for 30 minutes. To purify, the volume of the reactions was increased to 100 µl with TE, the reactions were P:C:P purified, and resuspended in 10 µl of TE.

PCR Amplification of Paired-Tag Library

PCR was performed at this stage to 1) increase the amount of library material that we have to work with, and 2) to eliminate extraneous ligation products in a single step. Without intending to be bound by theory, the only ligation products that should result from the PCR described in this step have tag-T30-tag flanked by properly oriented RDV2 and FDV2 on either side (note that the T30 segment itself is not symmetric, and therefore may be in either oriented in either direction relative to RDV2 and FDV2 segments).

As a complex mixture was being PCR-amplified, it was critical to stop the PCR reaction before primer molecules were exhausted. This is due to the fact that library molecules will begin to serve as primers for one another once the intended primers have run out, and that the library molecules contain enough similarity (~100 out of ~134 identical bases) such that after denaturing, it is unlikely that a given single-stranded library molecule will reanneal to its exactly complementary partner. The resultant library that has denatured and reannealed after primer has been exhausted can contain many "hybrid" library molecules.

PCR amplification was performed on a real-time PCR machine (OPTICON™ 2, MJ Research, Bio Rad, Waltham, Mass.).

TABLE 2

|  | Per 50 µl | ×20 (total volume of 1000 µl) |
|---|---|---|
| 10× PCR Buffer | 5 | 100 |
| 25 mM (each) dNTPs | 0.4 | 8 |
| 50 mM MgCl$_2$ | 1.5 | 30 |
| Platinum Taq | 0.2 µl | 4 |
| Water | 42.7 | 853 |
| RDV2-T (100 µM) | 0.1 | 2 |
| FDV2-T (100 µM) | 0.1 | 2 |
| SybrGreen (200×) | 0.0025 | 0.5 |

The master mix (set forth in Table 2) was split into two tubes of 499.5 µl, and 0.5 µl of library material ("M" or "R") was added to each. Each library's PCR was split into 8 tubes of 50 µl each (total volume of 400 µl) to run on the thermal cycler. Thermal cycling was performed as follows:

1. 94° C. for 2 minutes
2. 94° C. for 30 seconds
3. 55° C. for 30 seconds
4. 72° C. for 90 seconds
Go to step 2

Reactions were stopped after 15 cycles because the quantity of DNA was beginning to plateau. Reactions from each library were combined to individual tubes and purified with QIAQUICKS® (Qiagen, Valencia, Calif.) columns as per manufacturer's recommendations for PCR product purification. Resuspension was in 100 µl of Buffer EB. It was decided this was too high a volume for the next step, so the samples were ethanol precipitated (as in the P:C:P protocol except no phenol-extraction was done), washed and resuspended in 10 µl of TE.

PAGE Size-Selection of Paired-Tag Library

Reactions were run on a 6% PAGE gel. The 'final' library bands (sharp bands at approximately 135 base pairs) were cut, eluted and purified as previously. This was the last purification step—it was therefore critical to try and get as tight of a gel-purification as possible to minimize contamination from any non-library molecules that might be present. The PAGE gel was run with no ladders, as these molecules can also be frequent contaminants, and using a razor blade in a guillotine-type motion, rather than a scalpel.

Figure 16:
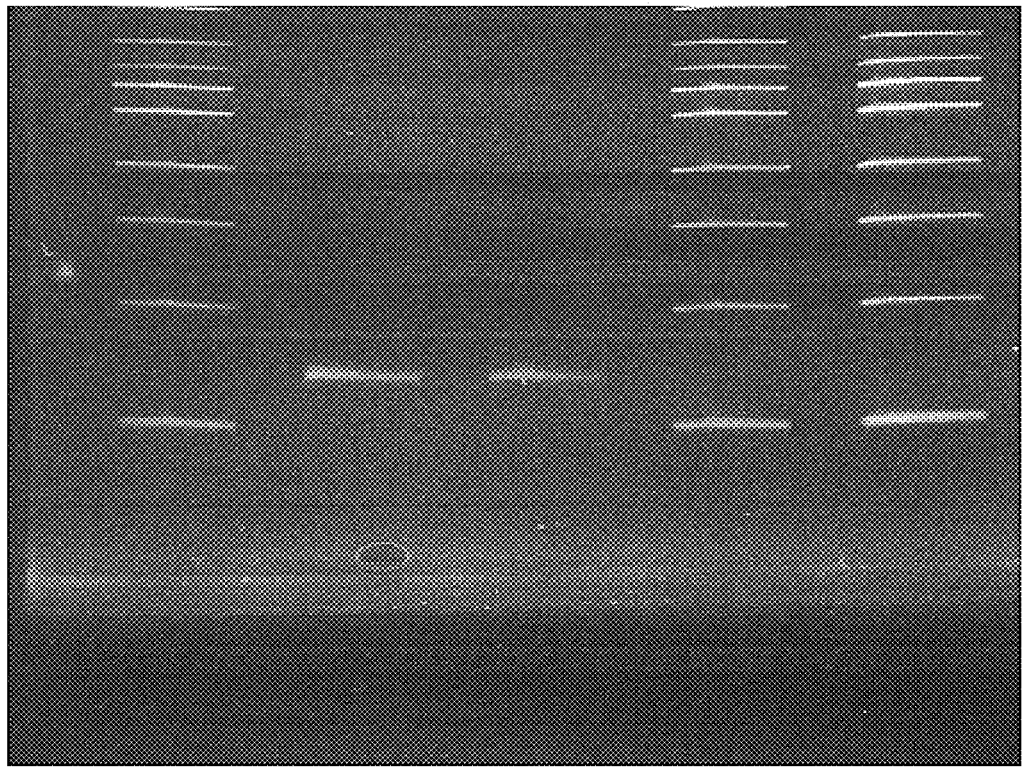
FIG. 16 depicts a diagnostic 6% PAGE gel of the final libraries.

After P:C:P purification with overnight precipitation, recovered library material was resuspended in 10 µl of TE. To quantify the library, a 6% PAGE gel with appropriate markers was run (FIG. 16). Based on relative intensities of library and ladder bands, concentrations were estimated at 2 ng/µl, resulting in approximately 9*2=18 ng of each library remaining. If the library was 135 bp, then the concentration was approximately 23 nM. The libraries were diluted in TE to various levels for use in emulsion PCR, and both the original libraries and their dilutions were stored at −20° C.

Library Validation Via Cloning and Sanger Sequencing

To validate the expectation that library tags would be E. coli derived and paired, "R"library fragments were cloned with the Invitrogen TOPO™-4 kit (Invitrogen, Carlsbad, Calif.) followed by PCR using M13F/M13R, and Sanger sequencing (single read per clone). Although 96 PCR products were submitted for sequencing, 20 of these came back as either garbage reads, or vector- or contaminant related. The remaining 76 inserts appeared be appropriately flanked by the RDV2 and FDV2 segments, as expected. Of these 76: one was a 6 bp insert (TTATCA); one was an E. coli genomic fragment (65 bp in length; 63/63 100% match to E. coli MG1655 genome on BLAST); one was an E. coli genomic fragment (70 bp in length; 69/69 100% match to E. coli MG1655 genome on BLAST); one contained the RDV2 primer flanked by ~27 bp with no significant matches in the NCBI data-base; and Seventy-two contained two tags separated by the T30 segment, as expected.

Of these 72, the tag lengths had the following distribution: 1 tag was 9 bp; 1 tag was 11 bp; 2 tags were 13 bp; 1 tag was 14 bp; 1 tag was 15 bp; 2 tags was 16 bp; 73 tags were 17 bp; 62 tags were 18 bp; and 1 tag was 22 bp. In terms of pairing, tags matched the E. coli genome as follows: 4 were situations where one or neither tag had any perfect matches to the E. coli genome (likely due to sequencing errors or non-canonical sequence); 1 was "unpaired" in that tags both matched unique locations but did not appear to originate from the same genomic regions; and 67 were matched the E. coli genome as paired tags (identically oriented with inter-tag distance falling within expected constraints). For these 67 paired tags, the distance distribution of the paired tags was 951+/−90 bp. The minimum distance was 729 bp and the maximum distance was 1162 bp.

Thus, the pairing rate for the 68 reads was 67/68, i.e., approximately 98.5%. A minimal estimate of the fraction of emulsion-PCR-amplifiable molecules in the library that represented paired E. coli tags with a T30 segment separating them was 67/76, i.e., 88%. The actual fraction could be slightly higher if the four reads where one or both tags were unmatchable actually did represent paired reads that were not matchable due to Sanger sequencing errors or differences between the "R" strain and the canonical genome sequence reference.

Although the sample size was small (n=72), deviations from 25/25/25/25 frequencies were observed in the tag sequences that may be significant trends (set forth in Table 3). The numbers in the first column represent the tag base position relative to either its junction with one or the other primer or with the T30 segment. The strand from which the base frequencies were tabulated is such that these frequencies are what one would expect to see if sequencing by extension from the primer or T30 segment (5' to 3'). Numbers in parentheses are the actual count-numbers (as opposed to frequencies).

TABLE 3

|  | A | G | C | T |
|---|---|---|---|---|
| PRIMER/TAG JUNCTION | | | | |
| +1 | 0.315 (45) | 0.315 (45) | 0.154 (22) | 0.217 (31) |
| +2 | 0.340 (49) | 0.104 (15) | 0.208 (30) | 0.347 (50) |
| +3 | 0.292 (42) | 0.208 (30) | 0.146 (21) | 0.354 (51) |
| +4 | 0.229 (33) | 0.250 (36) | 0.264 (38) | 0.257 (37) |
| +5 | 0.333 (48) | 0.194 (28) | 0.243 (35) | 0.229 (33) |
| T30/TAG JUNCTION | | | | |
| +1 | 0.299 (43) | 0.194 (28) | 0.326 (47) | 0.181 (26) |
| +2 | 0.299 (43) | 0.319 (46) | 0.146 (21) | 0.236 (34) |
| +3 | 0.312 (45) | 0.222 (32) | 0.222 (32) | 0.243 (35) |
| +4 | 0.188 (27) | 0.236 (34) | 0.264 (38) | 0.312 (45) |
| +5 | 0.252 (36) | 0.196 (28) | 0.273 (39) | 0.280 (40) |

EXAMPLE VII

Parallel Sequencing on Oligonucleotides Coupled to Beads

Figure 6:
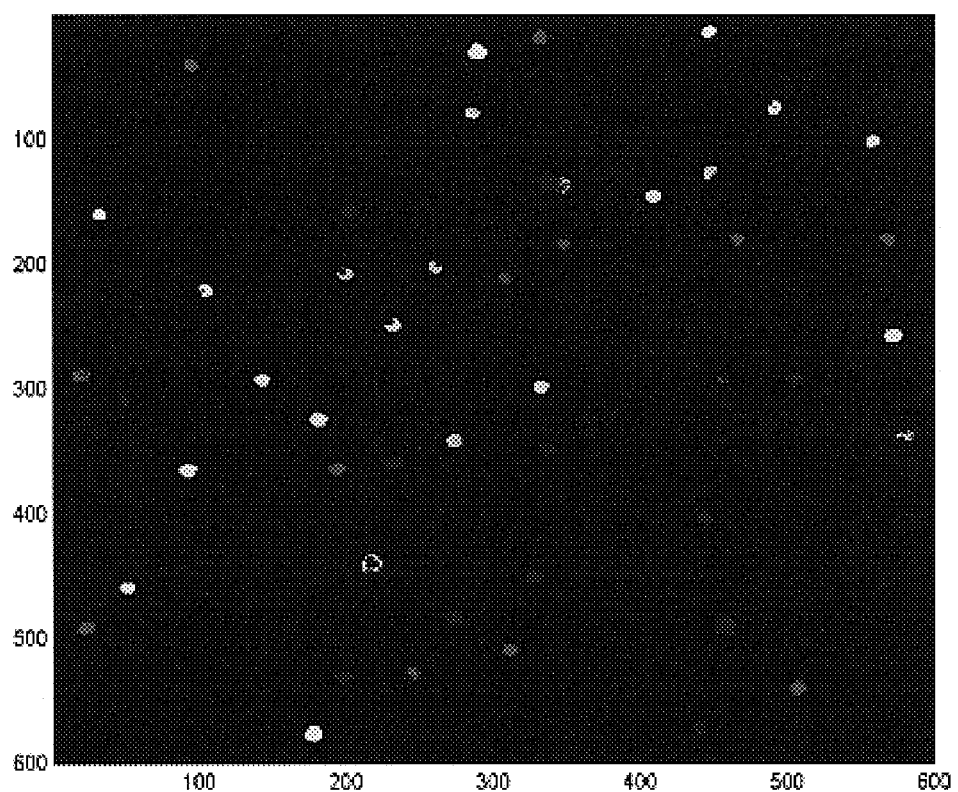
FIG. 6 depicts parallel sequencing on oligonucleotides coupled to 8.8-micron beads. A population of beads, each bearing one of five 80-mer oligonucleotides was immobilized in acrylamide and subjected to multiple rounds of fluorescent in situ sequencing (FISSEQ) until five to eight base-pair reads were obtained. This post-processing image shows a region of the slide, with pseudo-colors representing individual sequences (dark blue representing "noise signatures"). A 600×600-pixel region is shown, where the resolution is approximately 0.5 micron per pixel in each dimension. Images were acquired on an inverted epifluorescence microscope.

The results of an experiment in which 5 to 8 base-pair reads were obtained on oligonucleotides coupled via biotin to streptavidin-coated superparamagnetic beads (8.8 micron in diameter) are set forth in FIG. 6. The beads were immobilized in acrylamide. The beads set forth in FIG. 6 enable one of skill in the art to sequence 10,000 times more features per unit area on a single slide than using previously known methods.

Figure 7:
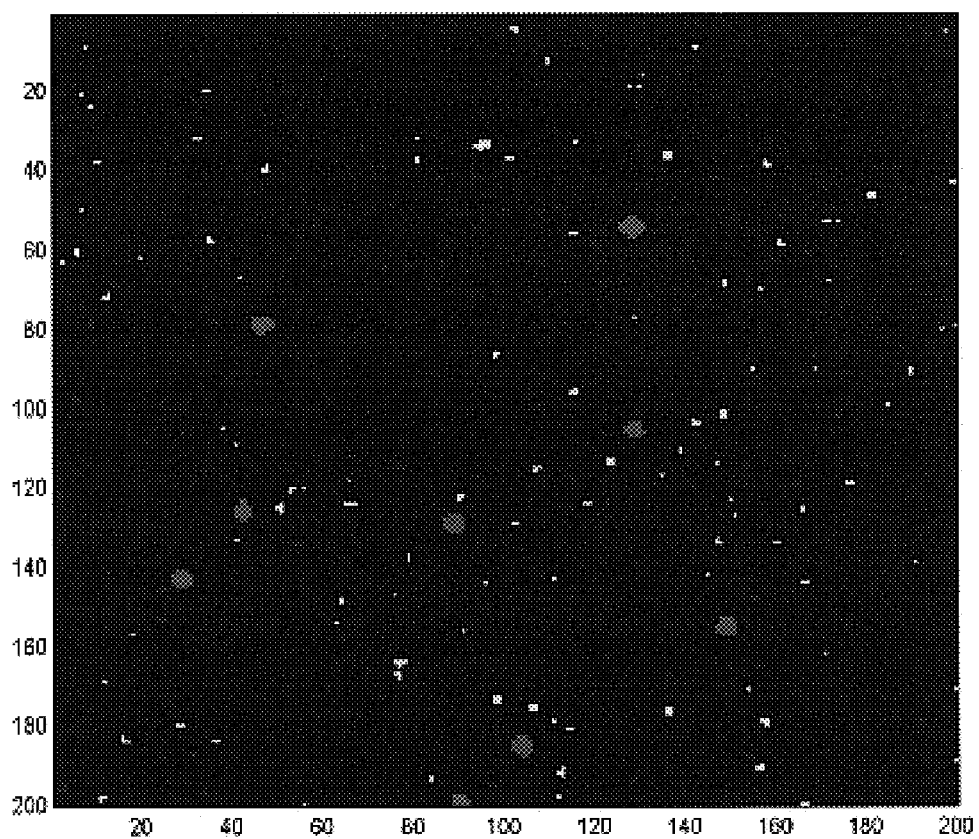
FIG. 7 depicts parallel sequencing on oligonucleotides coupled to 1 micron beads. A population of 1 micron beads, each bearing one of three 80-mer oligonucleotides was immobilized in acrylamide and subjected to multiple rounds of FISSEQ until four base-pair reads were obtained. Larger beads (2.8 micron) were mixed in to serve as fiduciary markers for image registration. Correct sequence signatures are pseudocolored red, white, yellow; noise signatures are pseudocolored dark blue; and fiduciary markers are pseudocolored green. A 200×200-pixel region is shown, where the resolution is approximately 0.5 micron per pixel in each dimension. Images were captured on an inverted epifluorescence microscope.

Towards further miniaturization, experiments were performed to generate short sequencing reads (4 base pairs per template) on 1-micron beads (FIG. 7). These results approach the resolution of "one sequence-read per pixel," as each bead was only represented by approximately 1 to 4 active pixels. At this demonstrated bead size and density, sequencing reads can be obtained from over 30 million independent beads per 1 inch by 3 inch microscope slide.

EXAMPLE VIII

Monolayers of Microspheres

A variation of the protocol set forth in Example III utilizes affinity in the self-assembled monolayers to provide for enrichment of the amplified beads. This avoids problems associated with current protocols for amplification. In such protocols, dilute target DNA is used to avoid double amplicons per bead and thus the number of beads with zero target DNA is approximated by a Poisson distribution.

The present invention also includes the use of similar emulsions to form sealed chambers (to limit spread of amplification) "in situ" on patterns of nucleic acids on slides (e.g., RNA in tissue sections, microarrays, stretched chromosomes). The use of an immobilized emulsion will also help constrain, stabilize and make more uniform distribution of emulsion droplet sizes.

Figure 8:
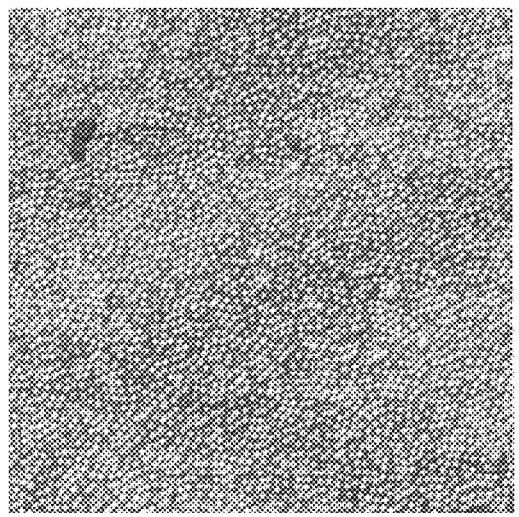
FIG. 8 depicts monolayers of paramagnetic polystyrene microspheres (1 micron diameter) prepared by convective self-assembly. The monolayers can be loosely packed (A) or more tightly packed (B) by varying the amount of detergent added.
Figure 8:
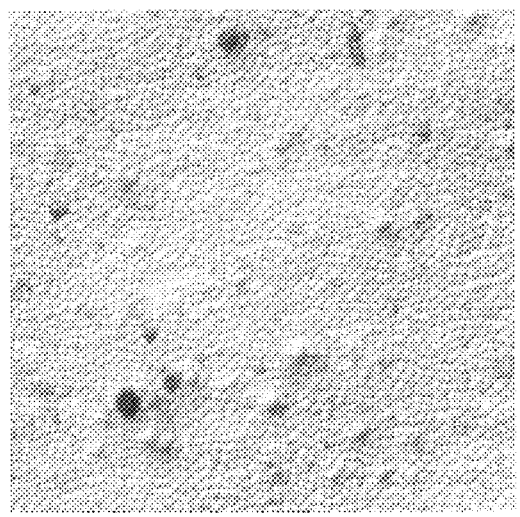
Figure 9:
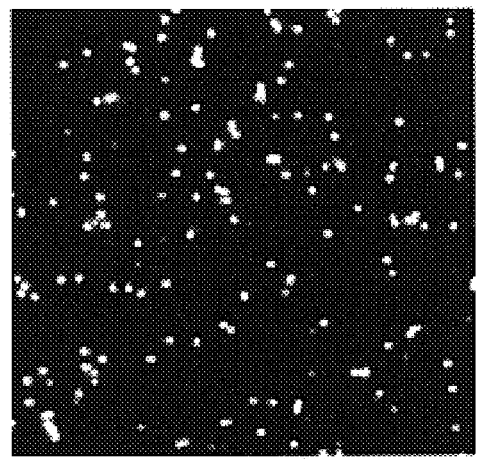
FIGS. 9A-9D depicts amplification of nucleic acids on particles without emulsions.
Figure 9:
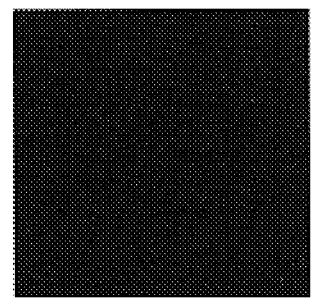
Figure 9:
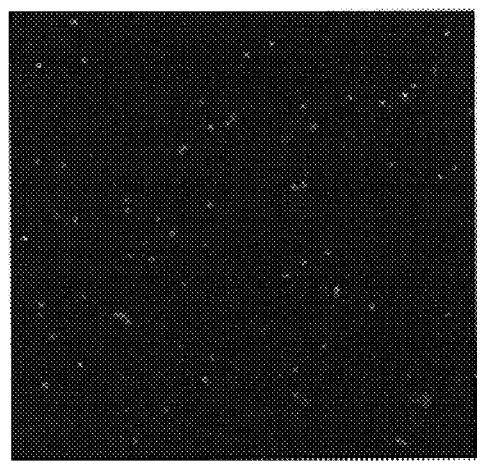
Figure 9:
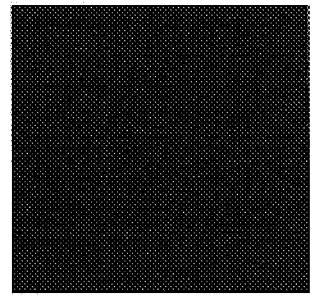

To obtain hundreds of millions to billions of independent sequencing reads per 1 inch by 3 inch microscope slide, the same 1-micron beads can be packed at high densities. Self-organizing monolayers (SOM) of superparamagnetic beads were generated (FIG. 8). Multilayers may also be constructed using transverse magnetic fields. Obtaining 30 base-pair reads from a slide perfectly coated with a monolayer of 1 micron beads would yield ~56 billion bases of sequence.

EXAMPLE IX

Amplification of Nucleic Acids on Particles without Emulsions

Without intending to be bound by theory, reducing feature size of polonies to micron or submicron sizes will improve the throughput at least 1000 fold. This can be achieved by restricting one amplification primer to polymer beads (such as 1 μm paramagnetic beads, available from Dynal, Oslo, Norway), polymer networks, or polymer nanostructures. Thus, the polony feature size is determined by the size of beads or polymeric matrix, and therefore is independent of the pore size and/or cross-linking content of polymeric matrix (acrylamide gel), and the length of target amplicons. Similar to conventional polony PCR, the actual amplification step for polony beads is carried out in a polymeric matrix (e.g. acrylamide gel), which helps to retain the location of individual beads and partially restrict the diffusion of amplicon. One important component of the present invention is the inclusion of additive (such as cationic lipid, polyamine, polycation, etc), which forms in-gel voids, e.g., micelles or aggregates, surrounding polymer beads and allows efficient amplification in a solid phase (FIGS. 9A-9D). The main advantage of this improvement is differential partitioning of target amplicon and the other amplification primer to the vicinity of the beads, which increases amplification efficiency and/or proximity to the bead. It avoids the necessity of forming emulsions and hence allows for simpler multiplex amplification and even the preservation of the 2D or 3D arrangement of the initial set of molecules to be amplified.

As an alternative, the second amplification primer can be immobilized to polymeric matrix (e.g., by acrydite modification or other crosslinking methods). Thus, little or no free second primer is required for amplification. This will eliminate crossover between beads during amplification and therefore enforce clonality. In addition to polymeric matrix (e.g., acrylamide gel), the formation of micelle or aggregate may further restrict the difflusion of free amplification products, if there are any (i.e., if there is residual free second amplification primer, or a free second primer is used during amplification). The mobility of a polyanion (e.g. DNA) within a polycationic layer (or network) can be fast relative to free diffusion away from the polycation and hence the reaction can be close to exponential until the cation layer is filled and then nearly come to a stop, further enhancing the sharpness of the subsequent images.

FIGS. 9A-9D depict copies of one amplification primer pre-coupled to 1-μm Dyna beads through biotin-streptavidin interaction. The other amplification primer is acrydite modified to permit it to be incorporated into a polyacrylamide gel matrix upon polymerization (left). Two primers, along with a nucleic acid amplification template of interest, were assembled in acrylamide matrix. PCR amplification was performed followed by denaturation and hybridization of Cy3-labelled probe. Few amplification products could be detected (right). In contrast to (left), when cationic lipid was added to the assembled mix and incubated for 15 minutes, the amplification efficiency was greatly enhanced as demonstrated by brighter signals.

EXAMPLE X

Analysis of DNA Modifications Using Polony Sequencing

The attachment of a methyl ($CH_3$) group to the 5' carbon of the cytosine residue in a CpG dinucleotide (which is referred to as an epigenetic modification) constitutes an important mechanism for controlling cellular gene expression. Quantitative knowledge on the dynamics of genomics methylation patterns will have great impact on biology, including developmental control and pathological states. Genome-wide detection of abnormal DNA methylation relies on restriction digestion with methylation-specific enzyme, followed by either differential display (MCA-RDA; Ueki et al. (2001) Cancer Res. 61:8540, incorporated herein by reference in its entirety for all purposes) or microarray analysis (DMH (Yan et al. (2000) Clin. Cancer Res. 6:1432), ECIST (Shi et al. (2002) Cancer Res. 62:3214, incorporated herein by reference in its entirety for all purposes). Though candidate differential methylation loci can be identified, none of them can monitor the combinatorial methylation events that are typical for any given CpG island. The only technology that can query the relationship of multiple methylations in cis is methylation-specific sequencing. However, the cloning of individual bisulfite-converted genomic fragments and performance of conventional sequencing procedures make that approach labor-intensive and low-throughput.

In one embodiment, the present invention is directed to adapting methylation-specific sequencing to the polony platform, imparting several advantages over the traditional methylation sequencing method. (1) Bisulfite-converted DNA fragments can be directly amplified in a solid or semi-solid phase (in this case, acrylamide), thus eliminating the requirement of laborious cloning step and potential bias introduced by differential cloning efficiency. (2) The detection of methyl-dC can be achieved in a highly-parallel manner such that thousands to millions of single molecules are queried simultaneously. Two approaches, repetitive probing and FISSEQ (Zhu et al. (2003) Science 301:836; Mitra et al. (2003) Analyt. Biochem. 320:55, incorporated herein by reference in their entirety for all purposes) can be applied to monitor differential methylation events. Whereas repetitive probing is suitable to study a handful of known loci, FISSEQ certainly has advantages for whole genome studies (see (4), below). (3) Because the polony platform is a single-molecule-based technology, little input material is required. Thus single cells and/or chromosomes may be utilized. Individual cells and/or chromosomes (e.g., a chromosome spread) can be embedded in polymer matrix or gel (e.g., polyacrylamide), followed by a solid-phase bisulfite conversion and amplification. This will eliminate DNA purification steps, and avoid the possible sample loss and contamination during sample preparation. (4) As an extension of (3), multiplex PCR and/or whole genome amplification (with, e.g., Phi29) can be performed with bisulfite-converted cells and/or chromosomes. This allows the determination of methylation status of the entire genomic DNA at a single cell and/or single chromosome level.

EXAMPLE XI

Fluorescence Resonance Energy Transfer (FRET)

By using two different fluorophore-labelled dNTPs which form a FRET donor-acceptor pair for a single FISSEQ step, e.g. Cy3-dATP donor plus Cy5-dATP acceptor, one can distinguish among zero, one and two identical bases in a homopolymer run. One excites first with the excitation wavelength of the donor dNTP and looks for emission at both the donor emission wavelength and the acceptor wavelength. One then excites with the acceptor excitation wavelength and looks for emission at the acceptor emission wavelength. One could reverse the order and first excite the acceptor to minimize photo-bleaching of the acceptor fluorophore as a result of FRET.

For example, if there are zero dA residues to be incorporated in a given cycle, then one will observe no (or low) signal. One dA will result in detection of the corresponding emission wavelength for each fluorophore excited as a result of FRET occurring. Two dAs will result in emission at the acceptor wavelength when excited at the donor excitation wavelength, as a result of FRET occurring. Three or more dAs can be determined as quantitative variants of the 2 dAs case.

EXAMPLE XII

Libraries

Libraries For Rolling Circles/Amplification

One method of generating a large library of circles directly from genomic DNA would be to use random N-mers at the ends and no internal tag for microarray hybridization such as: NNNNNN...(common primer 1)..(cut-site)..(common primer 2)..NNNNNN These N-mers may be used to hybridize randomly to DNA. Unlike the systems in the art, the N-mers could sit down at some distance from one another rather than with a single-base separation. This distance would be constrained by the length of the oligonucleotides utilized.

Polymerases, ligases and dNTPs may be used to gap-fill and ligate to generate a "padlocked" probe. Rather than releasing the pad-lock by recircularization, the genomic DNA may be digested with a restriction enzyme (with site not present in oligonucleotide) and exonuclease, leaving only circularized probes that contain a stretch of genomic bases. The circles could be used for the rolling circle method. Alternatively if the the emulsion method is being used, the padlock could be released via cleavage of the circle, leaving with genomic sequence flanked by common primers.

Jumping Libraries

This example sets forth one method by which a polony-ready library may be generated via phi29 rolling-circle amplimers. To generated a jumping library using MmeI (or EcoP15I) the following steps could be performed:

(1) Complete or partial cleavage of the genome with an endonuclease (e.g. NlaµI (CATGˆ) or CviJI** (NGˆCN) or even DNase; the 4 bp overhang may be the cleanest place to start);

(2) Optional size selection (the more precise the size selection, then the more precision in the assembly of sequences in complex repeat regions);

(3) Ligate a double-tag double-MmeI adapter, such that circles are formed;

(4) Optional size selection;

(5) Cut with MmeI, blunt and circularize again; and (6) The circles can be initiated into rolling circles by nicking randomly, by a sequence specific nicking enzyme, by strand invasion with DNA, PNA, RNA primers, or by RNA polymerase or Primase initiation.

This method will yield up to 27 base pairs of sequence information from each end, in addition to the information on the initial endonuclease sites (62 base pairs total for NlaIII) and more importantly allow assembly across longer de novo sequences.

Non-limiting examples of special restriction enzymes for used with non-rolling-circle libraries and non-rolling-circle libraries of the invention are as follows: SAGE: BsmFI, available from New England Biolabs (NEB), Beverly, Mass. (Velculescu et al. (1995) *Science* 5235 :484, incorporated herein by reference in its entirety for all purposes); LongSage: MmeI, available from NEB (Saha et al. (2002) *Nat Biotechnol.* 20:508, incorporated herein by reference in its entirety for all purposes); CAGE: MmeI, available from NEB (Shiraki et al. (2003) *Proc. Natl. Acad Sci. U.S.A.* 100:15776, incorporated herein by reference in its entirety for all purposes); SuperSage: EcoP 15I (Matsumura et al. (2003) *Proc. Natl. Acad. Sci. U.S.A.* 100:15718, incorporated herein by reference in its entirety for all purposes); SAGS: BsaXI, available from NEB (Torstein and Meyerson, Serial Analysis of Genome Subsets). BsmFI and EcoP15I have 5' overhangs, while MmeI has a 3' overhang. For MmeI the 3' 2 base pair information is preserved by ligating complementary pairs); and rapid shotgun cloning utilizing the two base recognition endonuclease CviJI (Fitzgerald et al. (1992) *Nucleic Acids Res.* 20:3753, incorporated herein by reference in its entirety for all purposes).

EXAMPLE XIII

Extensions of Excluded Volume

Figure 10:
FIG. 10 depicts a schematic of an excluded volume approach.
Figure 10:
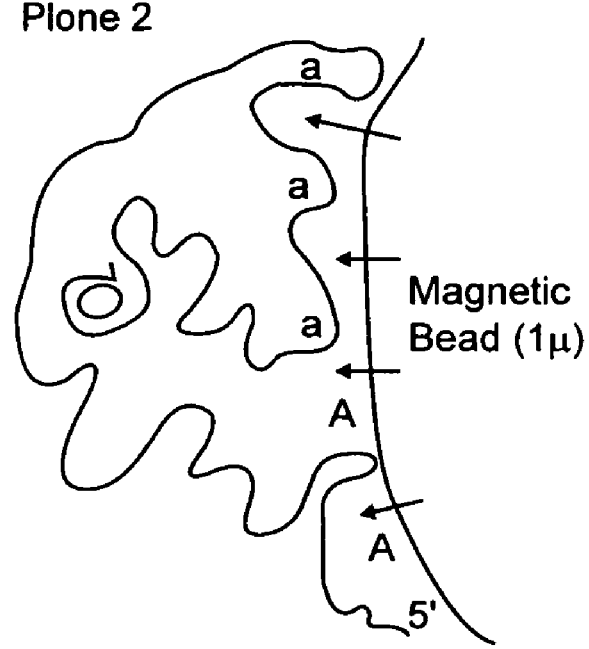

This example provides a means where clonal amplified beads can be generated with a high amplified bead:reaction volume ratio, without requiring PCR. One polymer (or particle) interacting with another can prevent further interactions with additional nearby particles. Template is pre-amplified by rolling circle amplification to yield long, voluminous concatemers. Thus, with excess of such template (FIG. 10) one can saturate all beads in the tube without multiple concatamer binding events per bead.

For example, with a library of 60-mer nicked circles, each having 30 base pairs of universal tags and 30 base pairs of insert sequence from a genomic library. A phi29 rolling circle (without any primers other than the nick) is used for about an hour until there are close to $1^4$ tandem single stranded repeats hanging off of the original circles. At low salt this will have a length of about $6^5$ bp (=200 microns extended) and an excluded volume of a few cubic microns. If a dilute solution of template interacts with 1-micron beads that carry complementary universal tags, then the first template to contact a bead will be bound at numerous points and exclude other templates from binding (set forth in FIG. 10). One can wash the beads at low salt (to reduce aggregation with other templates), then restart the rolling circle amplification (with only the bead bound primers). Without intending to be bound by theory, this should produce sufficient of single stranded template for sequencing (this may even produce more would be obtained by PCR since each primer will be bound to many tandem single-stranded repeats). This method should obviate the need for thermal cycling or bead sorting.

EXAMPLE XIV

References

Each reference is incorporated herein by reference in its entirety for all purposes.

Aach and Church (2004) *J. Theor. Biol.* 228:31
Merritt et al. (2003) *Nucleic Acids Res.* 31:e84
Mikkilineni et al. (2003) *Biotechnol. Bioeng.* 86:117
Mitra et al. (2003) *Anal. Biochem.* 320(1):55
Zhu et al. (2003) *Science* 301(5634):836
Butz et al. (2003) *BMC Biotechnol.* 31:11
Denkov et al. (1992) *Langmuir* 8:3183
Dressman et al. (2003) Proc. *Natl. Acad. Sci. USA* 100:8817
Brenner et al. (2000) Nat. *Biotechnol.* 18:630
Mitra et al. (2003) Proc. Natl. *Acad. Sci. USA* 100:5926
Mitra et al. (2003) *Anal. Biochem.* 320:55
Zhu et al. (2003) *Science* 301:836

---

What is claimed is:

1. An array comprising a plurality of beads, wherein an individual bead has a population of nucleic acid molecules having at least 50% sequence identity to each other attached thereto, which molecules differ in sequence from those of a population of nucleic acid molecules having at least 50% sequence identity to each other attached to another individual bead included in such plurality, and wherein the plurality of beads is immobilized in a semi-solid medium to form an array.

2. The array of claim 1, wherein the semi-solid medium is attached to a solid support.

3. The array of claim 2, wherein the support is a microscope slide or a flow cell.

4. The array of claim 2, wherein the semi-sold medium has top and bottom surfaces and the solid support is attached to the bottom surface.

5. The array of claim 1, wherein the individual beads comprise two, three or four different populations of nucleic acid molecules attached thereto, which molecules have at least 50% sequence identity to each other.

6. The array of claim 1, wherein at least 40% of the individual beads have populations of nucleic acid molecules attached thereto, wherein the nucleic acid molecules within each such population have at least 50% sequence identity to each other.

7. The array of claim 1, wherein the beads are immobilized as a monolayer.

8. The array of claim 1, wherein the semi-solid medium has x, y and z axes, and the plurality of beads is randomly arranged relative to the x and y axes.

9. The array of claim 1, wherein the semi-sold medium has top and bottom surfaces and the plurality of beads is immobilized near the top surface.

10. The array of claim 1, wherein the semi-solid medium is selected from the group consisting of: polyacrylamide, cellulose, polyamide, cross-linked agarose, cross-linked dextran and cross-linked polyethylene glycol.

11. The array of claim 1, wherein the plurality of beads comprises a plurality of clonal beads.

12. The array of claim 1, wherein the plurality of beads comprises a library.

13. The array of claim 1, wherein the nucleic acid molecules having at least 50% sequence identity to each other are primers.

14. The array of claim 1, wherein the nucleic acid molecules having at least 50% sequence identity to each other are amplified nucleic acid molecules.

15. The array of claim 1, wherein each of two, three or four individual beads has a population of nucleic acid molecules attached thereto having at least 50% sequence identity to each other.

16. The array of claim 15, wherein each population of nucleic acid molecules attached to each of the two, three or four individual beads differs in sequence from one another.

17. The array of claim 15, wherein each population of nucleic acid molecules attached to each of the two, three or four individual beads is identical in sequence to one another.

18. A method of producing an array comprising the steps of:
   a) providing a plurality of beads wherein an individual bead has a population of nucleic acid molecules having at least 50% sequence identity to each other attached thereto, which molecules differ in sequence from those of a population of nucleic acid molecules having at least 50% sequence identity to each other attached to another individual bead included in such plurality; and
   b) immobilizing the beads in a semi-solid medium to form an array.

19. The method of claim 18, further comprising attaching the semi-solid medium to a solid support in step b).

20. The method of claim 19, wherein the support is a microscope slide or a flow cell.

21. The method of claim 19, wherein the semi-sold medium has top and bottom surfaces and the solid support is attached to the bottom surface.

22. The method of claim 18, wherein the plurality of beads comprises two, three or four different populations of nucleic acid molecules attached thereto, which molecules have at least 50% sequence identity to each other.

23. The method of claim 18, wherein at least 40% of the individual beads have populations of nucleic acid molecules attached thereto, wherein the nucleic acid molecules within each population have at least 50% sequence identity to each other.

24. The method of claim 18, wherein the beads are immobilized as a monolayer.

25. The method of claim 18, wherein the semi-solid medium has x, y and z axes, and the plurality of beads is randomly arranged relative to the x and y axes.

26. The method of claim 18, wherein the semi-sold medium has top and bottom surfaces and the plurality of beads is immobilized near the top surface.

27. The method of claim 18, wherein the semi-solid medium is selected from the group consisting of: polyacrylamide, cellulose, polyamide, cross-linked agarose, cross-linked dextran and cross-linked polyethylene glycol.

28. The method of claim 18, wherein the plurality of beads comprises a plurality of clonal beads.

29. The method of claim 18, wherein the plurality of beads comprises a library.

30. The method of claim 18, wherein the nucleic acid molecules having at least 50% sequence identity to each other are primers.

31. The method of claim 18, wherein the nucleic acid molecules having at least 50% sequence identity to each other are amplified nucleic acid molecules.

32. The method of claim 18, wherein each of two, three or four individual beads has a population of nucleic acid molecules attached thereto having at least 50% sequence identity to each other.

33. The method of claim 32, wherein each population of nucleic acid molecules attached to each of the two, three or four individual beads differs in sequence from one another.

34. The method of claim 32, wherein each population of nucleic acid molecules attached to each of the two, three or four individual beads is identical in sequence to one another.

35. A method of producing an array comprising the steps of:
a) providing a plurality of beads wherein an individual bead has a population of nucleic acid molecules having at least 50% sequence identity to each other attached thereto, which molecules differ in sequence from those of a population of nucleic acid molecules having at least 50% sequence identity to each other attached to another individual bead included in such plurality;
b) immobilizing the beads in a semi-solid medium to form an array; and
c) amplifying the populations of nucleic acid molecules having at least 50% sequence identity to each other to form a plurality of beads having amplified populations of nucleic acid molecules having at least 50% sequence identity to each other attached thereto.

36. The method of claim 35, wherein the semi-solid medium includes an amplification primer.

37. The method of claim 35, wherein the semi-solid medium includes an additive that forms voids in the semi-solid medium.

38. The method of claim 37, wherein the additive is selected from the group consisting of: cationic lipid, polyamine and polycation.

39. The method of claim 35, wherein the nucleic acid molecules having at least 50% sequence identity to each other are primers.

40. The method of claim 35, wherein the nucleic acid molecules having at least 50% sequence identity to each other are amplified nucleic acid molecules.

41. A method of producing an array comprising the steps of:
a) providing a plurality of beads wherein an individual bead has a population of nucleic acid molecules having at least 50% sequence identity to each other attached thereto, which molecules differ in sequence from those of a population of nucleic acid molecules having at least 50% sequence identity to each other attached to another individual bead included in such plurality;
b) amplifying the populations of nucleic acid molecules having at least 50% sequence identity to each other to form a plurality of immobilized beads having amplified populations of nucleic acid molecules having at least 50% sequence identity to each other attached thereto; and
c) immobilizing the beads in a semi-solid medium to form an array.

42. The method of claim 41, wherein the amplifying is performed by emulsion PCR.

43. The method of claim 41, wherein the nucleic acid molecules having at least 50% sequence identity to each other are primers.

44. The method of claim 41, wherein the nucleic acid molecules having at least 50% sequence identity to each other are amplified nucleic acid molecules.

45. A method of producing an array comprising the steps of:
a) providing a plurality of beads wherein an individual bead has a population of nucleic acid molecules having at least 50% sequence identity to each other attached thereto, which molecules differ in sequence from those of a population of nucleic acid molecules having at least 50% sequence identity to each other attached to another individual bead included in such plurality;
b) amplifying the populations of nucleic acid molecules having at least 50% sequence identity to each other to form a plurality of beads having amplified populations of nucleic acid molecules having at least 50% sequence identity to each other attached thereto;
c) enriching the plurality of beads having amplified populations of nucleic acid molecules having at least 50% sequence identity to each other attached thereto to form an enriched population of beads; and
d) immobilizing the beads in a semi-solid medium to form an array.

46. The method of claim 45, wherein the nucleic acid molecules having at least 50% sequence identity to each other are primers.

47. The method of claim 45, wherein the nucleic acid molecules having at least 50% sequence identity to each other are amplified nucleic acid molecules.

48. A method for enriching a population of beads having a first nucleic acid molecule attached thereto comprising the steps of:
a) providing a population of beads wherein an individual bead has a population of nucleic acid molecules having at least 50% sequence identity to each other attached thereto, which molecules differ in sequence from those of a population of nucleic acid molecules having at least 50% sequence identity to each other attached to another individual bead included in such plurality;

b) contacting the population of beads with a second nucleic acid molecule immobilized on a support, wherein the second nucleic acid molecule has a sequence that is complementary to that of the first nucleic acid molecule;

c) incubating the population of beads and the second nucleic acid molecule together such that hybridization occurs to form a population of hybridized beads and a population of unhybridized beads; and d) separating the population of hybridized beads from the population unhybridized beads.

49. The method of claim 48, wherein the second nucleic acid is immobilized on a capture bead.

50. The method of claim 48, wherein the population of hybridized beads are separated from the population of unhybridized beads by density or affinity.

51. The method of claim 48, wherein the nucleic acid molecules having at least 50% sequence identity to each other are primers.

52. The method of claim 48, wherein the nucleic acid molecules having at least 50% sequence identity to each other are amplified nucleic acid molecules.

53. A kit containing an array comprising a plurality of beads immobilized in a semi-solid medium, wherein the plurality of beads includes an individual bead having a population of nucleic acid molecules having at least 50% sequence identity to each other attached thereto, which molecules differ in sequence from those of a population of nucleic acid sequences molecules having at least 50% sequence identity to each other attached to another individual bead included in such plurality.

* * * * *

SEQUENCE LISTING

```
<160> NUMBER OF SEQ ID NOS: 10

<210> SEQ ID NO 1
<211> LENGTH: 41
<212> TYPE: DNA
<213> ORGANISM: Artificial Sequence
<220> FEATURE:
<223> OTHER INFORMATION: Synthetic PCR primer
<220> FEATURE:
<221> NAME/KEY: misc_feature
<222> LOCATION: (1)..(1)
<223> OTHER INFORMATION: Dual biotin moieties

<400> SEQUENCE: 1
ccactacgcc tccgctttcc tctctatggg cagtcggtga t                41

<210> SEQ ID NO 2
<211> LENGTH: 23
<212> TYPE: DNA
<213> ORGANISM: Artificial Sequence
<220> FEATURE:
```

<223> OTHER INFORMATION: Synthetic PCR primer

<400> SEQUENCE: 2
ctgccccggg ttcctcattc tct                                          23

<210> SEQ ID NO 3
<211> LENGTH: 23
<212> TYPE: DNA
<213> ORGANISM: Artificial Sequence
<220> FEATURE:
<223> OTHER INFORMATION: Synthetic PCR primer

<400> SEQUENCE: 3
cctctctatg ggcagtcggt gat                                          23

<210> SEQ ID NO 4
<211> LENGTH: 69
<212> TYPE: DNA
<213> ORGANISM: Artificial Sequence
<220> FEATURE:
<223> OTHER INFORMATION: Synthetic capture primer
<220> FEATURE:
<221> NAME/KEY: misc_feature
<222> LOCATION: (1)..(1)
<223> OTHER INFORMATION: biotin moiety

<400> SEQUENCE: 4
cgtaccccgc ttggtctttc tcccgtaccc cgcttggtct ttctccctgc cccgggttcc   60
tcattctct                                                          69

<210> SEQ ID NO 5
<211> LENGTH: 31
<212> TYPE: DNA
<213> ORGANISM: Artificial Sequence
<220> FEATURE:
<223> OTHER INFORMATION: Synthetic T-tailed spacer oligonucleotide

<400> SEQUENCE: 5
gtcggaggcc aaggcggccg tacgtccaac t                                 31

<210> SEQ ID NO 6
<211> LENGTH: 31
<212> TYPE: DNA
<213> ORGANISM: Artificial Sequence
<220> FEATURE:
<223> OTHER INFORMATION: Synthetic T-tailed spacer oligonucleotide

<400> SEQUENCE: 6
gttggacgta cggccgcctt ggcctccgac t                                 31

<210> SEQ ID NO 7
<211> LENGTH: 43
<212> TYPE: DNA
<213> ORGANISM: Artificial Sequence
<220> FEATURE:
<223> OTHER INFORMATION: Synthetic PCR primer

<400> SEQUENCE: 7
aaccactacg cctccgcttt cctctctatg ggcagtcggt gat                    43

<210> SEQ ID NO 8
<211> LENGTH: 43
<212> TYPE: DNA
<213> ORGANISM: Artificial Sequence
<220> FEATURE:
<223> OTHER INFORMATION: Synthetic PCR primer

```
-continued

<400> SEQUENCE: 8
atcaccgact gcccatagag aggaaagcgg aggcgtagtg gtt                    43

<210> SEQ ID NO 9
<211> LENGTH: 25
<212> TYPE: DNA
<213> ORGANISM: Artificial Sequence
<220> FEATURE:
<223> OTHER INFORMATION: Synthetic PCR primer

<400> SEQUENCE: 9
aactgccccg ggttcctcat tctct                                        25

<210> SEQ ID NO 10
<211> LENGTH: 25
<212> TYPE: DNA
<213> ORGANISM: Artificial Sequence
<220> FEATURE:
<223> OTHER INFORMATION: Synthetic PCR primer

<400> SEQUENCE: 10
agagaatgag gaacccgggg cagtt                                        25
```